United States Patent [19]

Kelemen et al.

[11] Patent Number: 5,716,526
[45] Date of Patent: Feb. 10, 1998

[54] METHOD OF SEPARATING MATERIALS FROM LIPOSOMES OR LIPID COMPLEXES

[75] Inventors: Robyne J. Kelemen, Hamilton Township, N.J.; Anthony G. Durning, Yardley, Pa.

[73] Assignee: The Liposome Company, Inc., Princeton, N.J.

[21] Appl. No.: 599,869

[22] Filed: Feb. 12, 1996

Related U.S. Application Data

[63] Continuation of Ser. No. 442,073, May 16, 1995, abandoned, which is a continuation of Ser. No. 182,213, Jan. 14, 1994, abandoned.

[51] Int. Cl.$^6$ .......................... B01D 37/00; B01D 61/14
[52] U.S. Cl. .......................... 210/650; 210/483; 210/489; 210/490; 210/496; 210/651; 424/450; 436/177; 436/178; 436/829; 530/412; 530/414
[58] Field of Search .......................... 210/650, 651, 210/653, 506, 509, 483, 489, 490, 496, 656; 424/450; 436/177, 178, 829; 530/412, 414, 417

[56] References Cited

U.S. PATENT DOCUMENTS

| | | | |
|---|---|---|---|
| 4,522,803 | 6/1985 | Lenk et al. | 424/1.1 |
| 4,529,561 | 7/1985 | Hunt et al. | 264/4.3 |
| 4,588,578 | 5/1986 | Fountain et al. | 424/1.1 |
| 4,687,551 | 8/1987 | Furneaux et al. | 204/11 |
| 4,737,323 | 4/1988 | Martin et al. | 264/4.3 |
| 4,752,425 | 6/1988 | Martin et al. | 264/4.6 |
| 4,766,046 | 8/1988 | Abra et al. | 264/4.3 X |
| 4,861,580 | 8/1989 | Janoff et al. | 424/1.1 |
| 4,891,208 | 1/1990 | Janoff et al. | 424/1.1 |
| 4,897,384 | 1/1990 | Janoff et al. | 514/34 |
| 4,927,637 | 5/1990 | Morano et al. | 424/450 |
| 4,973,465 | 11/1990 | Baurain et al. | 424/406 |
| 5,008,050 | 4/1991 | Cullis et al. | 264/4.3 |
| 5,041,278 | 8/1991 | Janoff et al. | 424/1.1 |
| 5,077,056 | 12/1991 | Bally et al. | 424/450 |
| 5,082,664 | 1/1992 | Lenk et al. | 424/450 |
| 5,100,591 | 3/1992 | Leclef et al. | 264/4.6 |
| 5,242,595 | 9/1993 | Morgart et al. | 210/651 |

FOREIGN PATENT DOCUMENTS

| | | |
|---|---|---|
| 86/00238 | 1/1986 | WIPO. |
| 88/06443 | 9/1988 | WIPO. |
| 88/07850 | 10/1988 | WIPO. |
| 91/10422 | 7/1991 | WIPO. |
| 92/05772 | 4/1992 | WIPO. |

OTHER PUBLICATIONS

Alcoa, Life Sciences Technology, Manufacturer's LiteratureSterilox™Ceramic Membranes for Sterile Solutions, Illinois Water Treatment Company, 1990.

Alcoa, Life Seciences Technology, Manufacturer's Literature, "Membralox–LS Laboratory System", Illinois Water Treatment Company, 1988.

Alcoa Life Sciences Technology, Manufacturer's Literature, Membralox® Ceramic Membrane Laboratory Modules, Illinois Water Treatment Company, 1988.

Anotec Separations, Manufacturer's Literature, "Anotec Inorganic Membrane Filtration"., New York (1988).

Anotec Separations, Manufacturer's Literature, "Anotec Inorganic Membrane Technology Technical Bulletin 1"., New York (undated).

(List continued on next page.)

Primary Examiner—John Kim
Attorney, Agent, or Firm—Kenneth B. Rubin

[57] ABSTRACT

The invention provides a method of separating liposomes or lipid complexes from a fluidic medium. The method involves passage of a fluidic medium containing liposomes or lipid complexes through a composite filter which retains the liposomes or lipid complexes while allowing the fluidic medium to pass through. The filter is composed of a ceramic membrane and a ceramic substrate that is thicker than the ceramic membrane. Moreover, the average pore size of the ceramic membrane, from about 0.1 to about 0.2 microns, is less than the average pore size of the substrate.

12 Claims, 11 Drawing Sheets

OTHER PUBLICATIONS

Bangham, et al., "Diffusion of Univalent Ions Accross the Lamellae of Swollen Phospholipids", J. Mol. Bio., 13:238–252 (1965).

Bhave, r. *Inorganic Membranes Synthesis, Characteristics and Applications*, Chapman & Hall Publishers, New York, pp. 10–17, 26, 34–39, 45–49, 55–56, 64–94, 144–147, 128–140, 295–298 (1991).

Cheryan, M. *Ultrafiltration handbook*, Technomic Publishing Co., Inc.Lancaster, PA, 1986, pp. 205–213.

Deamer, et al., "Liposome Preparations: Methods and Mechanisms", in *Liposomes*, edited by M. Ostro, Marcel Dekker, Inc., New York pp. 27–51 (1983).

Deamer, et al., "Large Volume Liposomes by an Ether Vaporization Method", Biochemica et Biophysica Acta, 443:629–34 (1976).

Fifield, "Sterilization Filtration", in *Disinfection, Sterilization, and Preservation*, 2nd Edition, edited by S. Block, Lea & Febiger, Philadelphia, pp. 562–591 (1977).

Furneaux, et al., "The Formation of Controlled–Porosity Membranes from Anodiaclly Oxidized Aluminium":, *Nature*, 337:147–9 (1989).

Hoffman, "Inorganic Membrane Technology in Sample Preparation", *American Laboratory News Edition*, Apr., 1989.

Illinois Water Treatment Company, Manufacturer's Literautre, "Sterilox ™Ceramic Membranes For Sterile Solutations", Rockford, IL (undated).

Jones, et al., "Comparison of a new Inorganic Membrane Filter (Anopore) with a Track–Etched Polycarbonate Membrane filter (Nuclepore) for Direct Counting of Bacteria", *Applied and Environmental Microbiology*, 55(2):529–30 (1989).

Kolb, et al., "The Ins and Outs of Coating Monolithic Structures", Chemical Engineering Progress, Feb., 1993, 61–67.

Millipore, Manufacturer's Literature, "Solve Tough Process Filtration Problanes with Ceraflo Ceramic Systems", Bedford, MA (1989).

Papahadjapoulos, et al., "Phospholipid Model Membranes I. Structural Characteristics of Hydrated Liquid Crystals", Biochim. Biophys. Acta, 135:624–638 (1967).

RP Tech–Sep Groupe Rhone–Poulenc Manufacturrer's Literature, "Carbosep® micro and ultrafiltration", Miribel Cedex, France (undated).

Sartorius, Manufactuer'r Literature, "EasyFlow, The Easy-–to–Use Disposable Crossflow Device", Bohemia, NY (undated).

Sartorius, Manufactuer'r Literature, "Process Filtration Life Sciences", Bohemia, NY (undated).

Sartorius, Manufactuer'r Literature, "Sartorius Filter Cartridges", Bohemia, NY (undated).

Schullery, et al., "Studies on Phosphatidylcholine Model Membranes–Size–Heterogeneity Effect on Permeability Measurements", *Chem. Rhys. Lipids*, 12:75–95 (1973).

Szoka, et al., "Procedure for preparation of Liposomes with large internatl aqueous space and high capture by revverse–phase evaporation", *Proc. natl., Acad. Sci., USA*, 75(9):4194–8 (1978).

Szoka, et al., "Comparative Properties and Methods of Preparation of Lipid vesicles (Liposomes)", *Ann. Rev. Biophys. Bioeng.,*, 9:467–508 (1980).

U.S. Filter Corporation, Manufacturer's Literature, "Membralox® Ceramic Membrane Filtration Products", Warrendale, PA (1992).

U.S. Filter Corporation, Manufacturer's Literature, "Membralox® Ceramic Membranes", Warrendale, PA (1992).

24          24

30

30

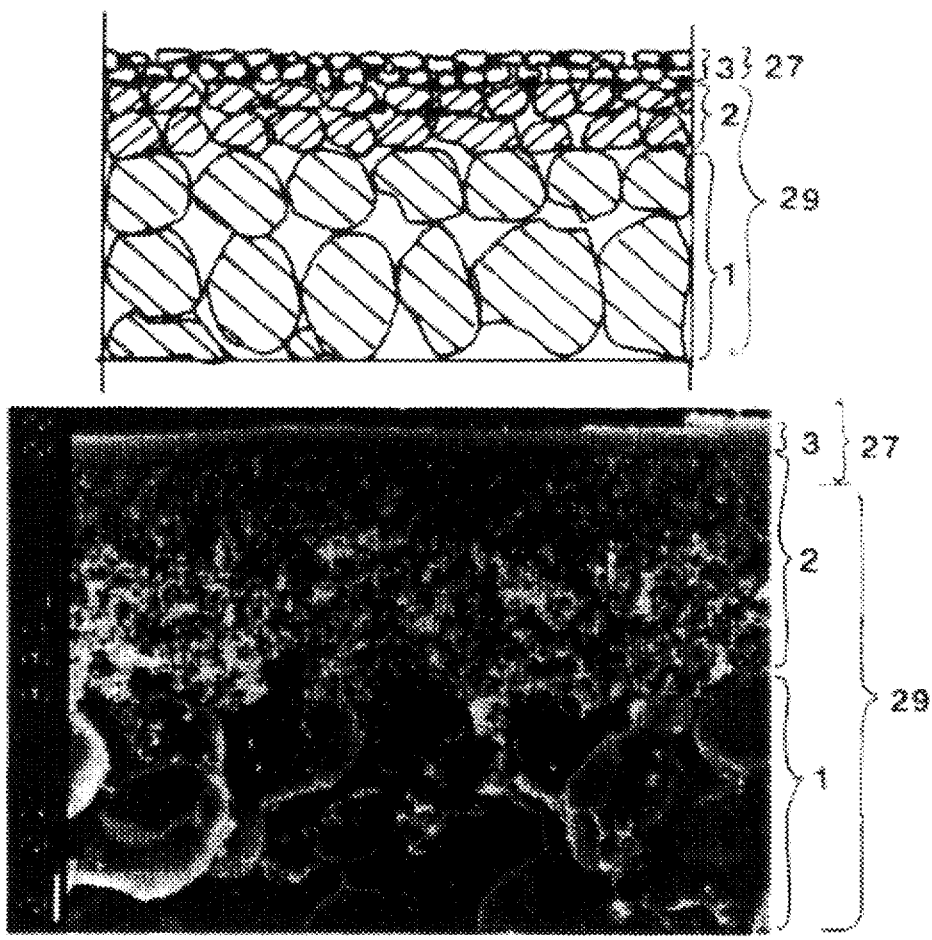

} 3

} 3

} 3
          4

METHOD OF SEPARATING MATERIALS FROM LIPOSOMES OR LIPID COMPLEXES

This application is a continuation of U.S. Ser. No. 08/442,073, filed May 16, 1995, now abandoned, which-in-turn is a continuation of U.S. Ser. No. 08/182,213, filed Jan. 14, 1994, now abandoned.

This invention is directed to methods of separating liposomes and lipid complexes from a fluid containing them. More particularly, this invention involves the use of a composite filter having a membrane and a substrate, wherein the membrane has a smaller thickness and nominal pore size than the substrate.

There are several ways to separate substances from within a fluid, such as dialysis, centrifugation, and filtration. The present invention is directed toward methods of separation using filtration.

Diafiltration, a preferred embodiment of the present invention, is a filtration technique in which permeable solutes are removed by the addition of fresh solvent or other solution to the feed liquid. The remaining liquid (the retentate) containing non-permeated substances is either discarded or recycled to the feed source. Diafiltration systems employ a filter having a rated pore size such that generally materials having a size equal to or less than the rated pore size will be able to pass through the filter material.

The present invention is directed to filtration of liposomes and lipid complexes. Liposomes are lipid-based vesicles composed of one or more bilayers, each of which contains two layers of amphipathic lipid molecules whose polar headgroups are oriented towards the internal aqueous compartment(s) or towards the external aqueous medium, and whose hydrophobic fatty acid chains are pointed towards the hydrophobic bilayer interior.

Once liposomes have been formed, it is generally desirable to separate the population of liposomes from the starting materials used to form the liposomes, particularly when the starting materials include a hydrophilic bioactive agent. The separation process for removal of the starting materials including the unassociated bioactive agent is preferably conducted under a high flux rate, resulting in only minor leakage of lipid or liposomes across the filter while maintaining the integrity of the retentate.

Filters customarily employed in diafiltration systems are made from fibrous materials such as polypropylene, cellulose, polysulfone, polytetrafluroethylene (teflon), and the like. The fibrous materials, however, are disadvantageous for commercial use, for example, because they must be discarded after only a limited number of uses, they are compressible, and they are costly.

It is therefore desirable to improve, for example, the efficiency and commercial feasibility of separation of liposomes or lipid complexes from starting materials, by employing a filter which, inter alia, allows filtration at superior flux rates, requires less frequent replacement, and is able to effectively separate materials such as unassociated bioactive agent from the liposomes or lipid complexes.

SUMMARY OF THE INVENTION

The present invention provides methods of separating liposomes or lipid complexes from a fluid containing the same by passing the fluid through a composite filter. The filter has a substrate and a membrane thereon having a smaller thickness and nominal pore size than the substrate. In certain embodiments, the substrate comprises more than one layer. Also, in certain embodiments, the membrane comprises more than one layer.

In preferred embodiments, the substrate is a ceramic, such as an aluminum oxide. In other preferred embodiments, the substrate is carbon. In further embodiments, the substrate is a porous metal, such as stainless steel, silver, nickel, Monel, Hastelloy or Iconel, and preferably stainless steel. In additional embodiments, the substrate is a porous glass. In preferred embodiments, the membrane is selected from the group consisting of aluminum oxides zirconium oxide and titanium oxide, and most preferably, zirconium oxide. In other embodiments, the substrate and/or membrane are yttrium oxide, thorium oxide, and beryllium oxide.

In certain preferred embodiments, the thickness of the membrane is from about 0.001 to about 0.020 mm, and more preferably, about 0.001 to about 0.010 mm, and even more preferably, about 0.002 to about 0.005 mm. Additionally, in preferred embodiments, the nominal pore size of the membrane is up to about 10%, and preferably from about 5 to 10% of the mean particle size of the liposomes or lipid complexes. In preferred embodiments, the nominal pore size of the membrane is from about 0.05 to about 0.2 microns. In further preferred embodiments, the membrane has a nominal pore size of about 0.1 micron.

In certain preferred embodiments, the thickness of the substrate is from about 1.0 to about 2.0 mm. This thickness preferably includes multiple layers, preferably at least some of which have a thickness of about 10 to about 50 μm.

In preferred embodiments, such as the methods provided in the examples, the filter has an average transmembrane pressure of about 10 p.s.i. to about 30 p.s.i., and more preferably, an average transmembrane pressure of about 20 p.s.i. Preferably, the fluid has a recirculation cross-flow velocity of about 3 to about 7 m/sec. Further, preferably, there is no backflushing of filtrate flow.

The methods of the present invention can be used, for example, with liposomes that have an associated bioactive agent, such as a hydrophilic drug, for example, an aminoglycoside. Examples of aminoglycosides include but are not limited to gentamicin, streptomycin, dihydrostreptomycin, tobramycin, neomycin B, paromycin, ribostamycin, lividomycin, kanamycin, viomycin, sisomicin, netilimicin and amikacin, and most preferably, gentamicin.

The methods of the present invention can also be used, for example, with lipid complexes that have an associated hydrophobic bioactive agent, such as a polyene macrolide antibiotic. Examples of polyene macrolide antibiotics include but are not limited to nystatin, pimaricin, candicidin, filipin, and most preferably, amphotericin B.

BRIEF DESCRIPTION OF THE DRAWINGS

The following drawings are illustrative of embodiments of the invention and are not intended to limit the invention as encompassed by the claims forming part of the application.

FIG. 2c is a schematic representation of supported, asymmetric pores. See Bhave, *Inorganic Membranes*, at page 12.

FIG. 2d is a scanning electron micrograph of an example of a filter with supported, asymmetric pores.

FIG. 5b is a schematic, partial cross-sectional view of the entire filter shown in FIG. 5a.

DETAILED DESCRIPTION OF THE INVENTION

The present invention is directed to processes for separating liposomes or lipid complexes from a fluid containing the same. A lipid complex is defined as a lipid aggregate, other than a liposome, which comprises a lipid:bioactive agent: complex in non-liposomal particulate form, wherein the molar ratio of lipid to bioactive agent is less than that above which only liposomes will form. The process of the present invention is particularly suited, for example, to the separation of liposomes or lipid complexes having an associated bioactive agent from by-products of their manufacture, including separation of unassociated bioactive agent and free lipid, especially when the bioactive agent is hydrophilic and thus less likely to associate with the lipid when it is unentrapped.

The separation methods of the present invention involve utilizing a composite filter comprised of a substrate and a membrane thereon having a lower pore size and thickness than the substrate. A "composite filter", as the term is used herein, is defined as a filter having at least two integral components, namely, a membrane and a substrate. Types of composite membranes are described in R. Bhave, *Inorganic Membranes: Synthesis, Characteristics and Applications* (Van Nostrand Reinhold 1991), relevant portions of which are hereby incorporated herein by reference.

In preferred embodiments, the nominal pore size of the membrane is smaller than that of the substrate. In further preferred embodiments, the nominal mean pore size of the membrane is smaller than that of the substrate. "Nominal mean pore size" as used herein means that individual filters of a population of filters made by the same manufacturer have a pore size within a continuous range of pore sizes which encompass a mean pore size. The term "nominal pore size" means that the filters are rated by their average pore size, and an individual pore size can be higher or lower than the rated pore size. The term "sterilizing porosity" means that the pore size of the filter is not above the rated pore size.

The membrane and substrate each can have more than one layer. The membrane functions to separate the liposome or lipid complex from other material, and the membrane preferably covers the substrate on the feed side of the filter. The substrate does not function to separate the liposome or lipid complex from other materials, and preferably provides mechanical strength to the membrane. Preferably, the membrane has defect-free physical integrity.

Figure 4A:
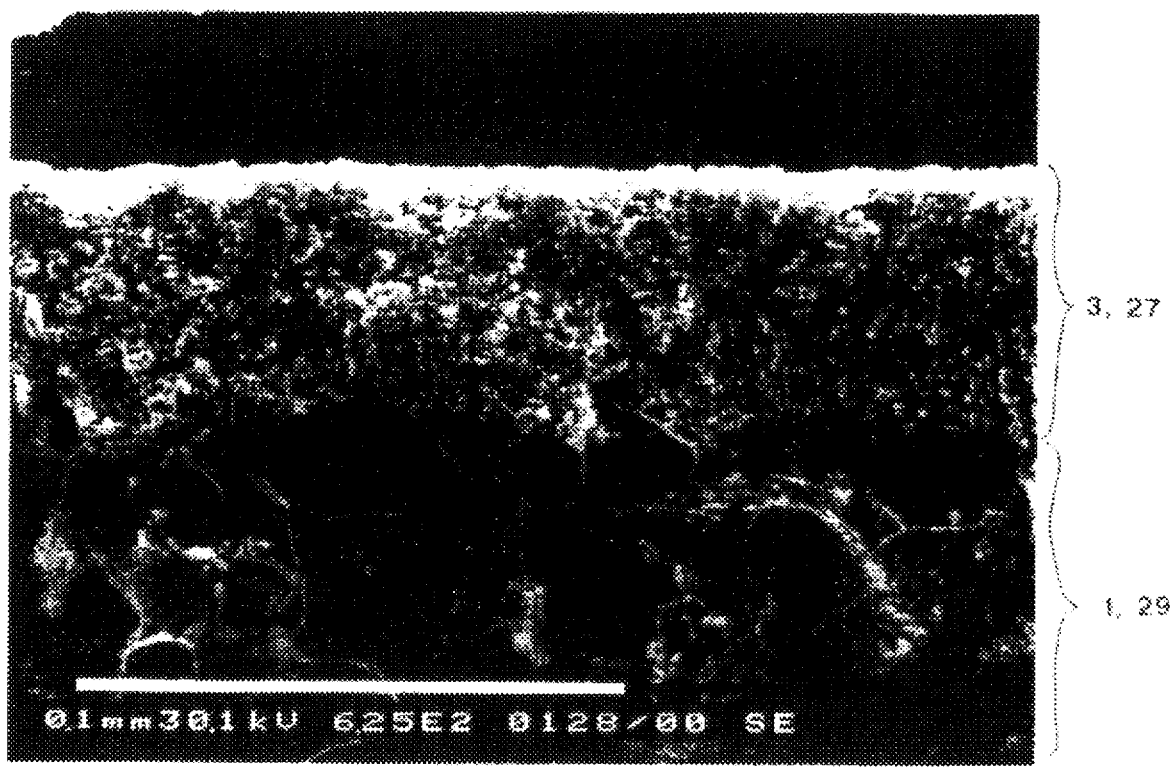
FIG. 4a depicts a scanning electron micrograph of the cross-section of an aluminum oxide composite filter with one layer of support that can be used in accordance with the methods of the present invention. See Bhave, *Inorganic Membranes*, at page 69.
Figure 4B:
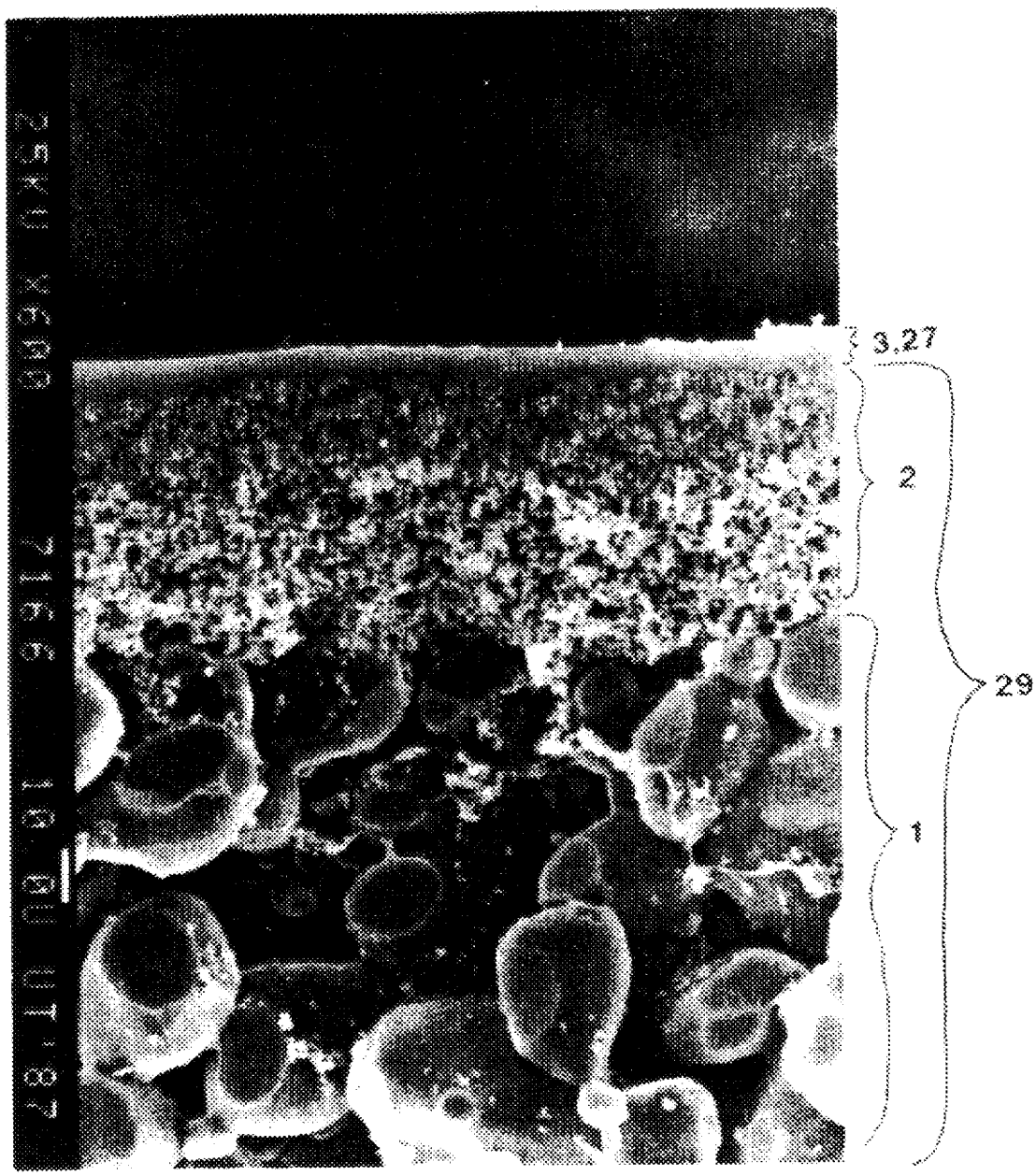
FIG. 4b depicts a scanning electron micrograph of the cross-section of an aluminum oxide composite filter with three layers of support that can be used in accordance with the methods of the present invention. See Bhave, *Inorganic Membranes*, at page 70.

The membrane can have more than one layer, for example, when it has more than one layer with pore sizes that serve to filter out liposomes or lipid complexes. Preferably, the membrane has one layer. The substrate layer can have more than one layer, for example, when it has more than one layer with pore sizes that do not serve to filter out liposomes or lipid complexes, and preferably the substrate layer(s) do not cause resistance. In certain preferred embodiments, the substrate has one layer, and in other preferred embodiments, the substrate has more than one layer; for example, 2–10 layers, and preferably, 2 or 3 layers. Multiple layers within the substrate are preferred in certain embodiments, for example, to prevent collapse of the of the membrane during its synthesis, to prevent collapse of a thin membrane into large pores of a substrate, and to regulate the pressure drop across the top layer of the membrane during filtration. See FIGS. 1a, 2c, and 3 for schematic diagrams of composite membranes. See FIGS. 2d, 4a and 4b for micrographs of filters having a one-layered substrate (4a) and a multi-layered substrate (2d and 4b) that can be used in accordance with the methods of the present invention. Specifically, the filters in FIGS. 2d and 4b have a substrate 29 with two layers, 1 and 2, and a membrane 27 with a single layer 3. In contrast, the filter in FIG. 4b has a substrate 29 with a single layer 1.

Where either the membrane or the substrate has more than one layer, the pore size is defined as that of the layer having the smallest pore size. Preferably, the layer having the smallest pore size is on the feed side of the filter, and preferably, the pore size of the layers become sequentially smaller as the layers progress to the feed side of the filter. See, for example, FIG. 2d, in which the pore size of the layers becomes progressively smaller from substrate layer 1 to substrate layer 2 to membrane layer 3.

Additionally, where either the membrane or the substrate has more than one layer, the thickness is defined as that of the total sum of all layers in the membrane or substrate.

The thickness and pore size of the substrate will depend on the substrate material and on the material to be filtered. For aluminum oxide ceramic substrates, the thickness is typically about 1 to about 6 mm and the nominal mean pore size is from about 2 to about 10 microns.

The layer of the substrate closest to the feed side is coated with a membrane, preferably of aluminum oxide, zirconium oxide or titanium oxide, and most preferably with zirconium oxide. The selection of a suitable pore size and thickness for the membrane is dependent in part on the particle size of the liposomes or lipid complexes which are to be separated. Also, the thickness of the membrane is less than that of the substrate, and preferably is equal to or less than about 1 to about 20% of the thickness of the substrate, and most preferably, as thin as technically possible.

In general, a mean pore size for the membrane of up to about 10%, and preferably about 5 to about 10% of the mean particle size of the liposomes or lipid complexes is preferred for a diafiltration filter to minimize the passage of the liposomes or lipid complexes through the filter while maximizing the flux of the diafiltration solvent. "Mean particle size" is defined as the mean outside diameter of the liposomes or lipid complex. Liposomes or lipid complexes may have size ranges, for example, of 30 nm to 50 µm. Generally, the liposomes used in the examples have a mean particle size of about 3 to about 5 µm. For illustration, in the preparation of liposomes or lipid complexes having a size range for example, of about 1,000 to 5,000 nm, the nominal pore size of the membrane will preferably be in the range of from about 50 to 500 nm, preferably about 100 to 300 nm.

It will be understood by one skilled in the art that not all of the liposomes or lipid complexes need to be retained by the filter, (in the "retentate"), so long as a substantial amount and preferably, substantially all of the liposomes or lipid complexes are retained. The liposome or lipid complex preparation can contain a range of liposome or lipid complex sizes such that the smaller liposomes or lipid complexes do pass through the filter.

In certain embodiments, the nominal pore size of the filter is about 2 to about 10 microns. In preferred embodiments, the nominal pore size of the filter is about 0.05 to about 10 microns, more preferably, about 0.05 to about to about 2 microns, even more preferably, about 0.05 to about 1 micron, and most preferably, about 0.1 micron. The pore size is preferably sufficient small to avoid leakage of larger liposome or lipid complexes but sufficiently large to avoid the requirement of higher pressure and additional cleaning.

The thickness of the membrane is dependent on its method of formation and in certain preferred embodiments, is as thin as technically possible, and preferably from about 0.001 to about 0.02 mm, and more preferably about 0.002 to about 0.005 mm. Zirconium oxide is a preferred membrane material because, inter alia, it can be applied to the substrate in very thin layers such as 0.005 mm and less. Generally, increasing the thickness of the membrane causes a corresponding decrease in flux rate.

A membrane can be layered on a substrate, for example, according to Kolb, et al., *Chem. Eng. Proc.*, Feb. 1993, 61–67, which is hereby incorporated herein by reference. The membrane can be made of a different material than the substrate, or it can be made of the same material as the substrate with different characteristics, including thickness and pore size. Furthermore, in those embodiments in which the membrane and/or substrate have multiple layers, the layers within the membrane or substrate can be made of different materials. Examples of coated filters include, but are not limited to, Sterilox™ ceramic membranes (Illinois Water Treatment Co., Rockford, Ill.), Membralox™ ceramic membranes (Illinois Water Treatment Co., Rockford, Ill.), and Carbosep® membranes (Groupe Rhone Poulenc, Cedex, France). In preferred embodiments, the membrane is selected from the group consisting of metallic oxides, preferably, aluminum oxide, zirconium oxide and titanium oxide, and most preferably, zirconium oxide. Oxide ceramic materials are used in preferred embodiments since, for example, nonoxide ceramic materials do not tolerate exposure to oxidizing environments, particularly at high temperatures. Other oxide ceramics that can be used include, for example, ruthenium oxide and cerium oxide. It has been found that the use of composite porous filters according to the present invention allows the separation of permeable solutes from liposomes or lipid complexes at greater flux rates than uncoated filters. Improvement of the flux rate, for example, reduces production time and makes the processing of liposomes or lipid complexes more cost effective.

In certain embodiments, the membrane can be modified, for example, by providing multiple layers within the membrane pores, partial plugs in the pores, and partial plugs or layers on top of the pores. See, for example, FIG. 3, which provides schematic representation of a modification of pores within the layer 3 of the membrane 27 wherein the modifications are in part a, homogeneous layers in the pores, part b, partial plugs in the pores, and part c, layer(s) or partial plugs (4) on top of the pores. Materials that can be used for such modifications include, for example, magnesium oxide, vanadium oxide and silicon oxide. See, for example, Bhave, *Inorganic Membranes* at pages 14 and 56.

In preferred embodiments, the substrate and/or membrane is a ceramic, preferably a metal oxide, such as aluminum oxide. In other preferred embodiments, the substrate is carbon. In further embodiments, the substrate and/or membrane is a porous metal, such as stainless steel, silver, nickel, Monel, Hastelloy or Iconel, and preferably stainless steel. In additional embodiments, the substrate and/or membrane is a porous glass. For example, silicon oxide and silicon carbide may be used. In other embodiments, the substrate and/or membrane are silicon oxide, yttrium oxide, thorium oxide, and beryllium oxide. For examples of commercially available porous filters, see Table 1. The filters that have both a membrane and substrate (support) illustrate commercially available filters that may be used in accordance with the methods of the present invention. It will be understood by one skilled in the art that filters which may be developed in the future that have a substrate and a membrane wherein the membrane has a smaller thickness and nominal pore size than the substrate may also be used in accordance with the present invention.

TABLE 1

Commercial Porous Inorganic Membranes

| Manufacturer | Trade Name | Membrane Material | Support Material | Membrane Pore Diameter | Geometry of Membrane Element | Tube or Channel Inside Diameter (mm) |
|---|---|---|---|---|---|---|
| Alcoa/SCT | Membralox ® | $ZrO_2$ $Al_2O_3$ | $Al_2O_3$ $Al_2O_3$ | 20–100 nm 0.2–5 μm | Monolith/ Tube | 4 and 6 |
| Norton | Ceraflo ® | $Al_2O_3$ | $Al_2O_3$ | 0.2–1.0 μm 6 μm (symmetric) | Monolith Tube | 3 |
| NGK | | $Al_2O_3$ | $Al_2O_3$ | 0.2–5 μm | Tube | 7 and 22 |
| Du Pont | PRD-86 | $Al_2O_3$ Mullite, Cordierite | None | 0.06–1 μm | Tube | 0.5–2.0 |
| Alcan/Anotec | Anopore ® | $Al_2O_3$ $Al_2O_3$ | $Al_2O_3$ $Al_2O_3$ | 20 nm 0.1 μm 0.2 μm | Plate | |
| Gaston County Filtration Systems | Ucarsep ® | $ZrO_2$ | C | 4 nm | Tube | 6 |
| Rhone-Poulenc/SFEC | Carbosep ® | $ZrO_2$ $ZrO_2$ | C C | ~4 nm 0.08–0.14 μm | Tube | 6 |
| Du Pont/ CARRE | | $Zr(OH)_4$ | SS | 0.2–0.5 μm | Tube | ~2 |
| TDK | Dynaceram ® | $ZrO_2$ | $Al_2O_3$ | ~10 nm | Tube | Ld5 |
| Asahi Glass | | Glass | None | 8 nm–10 μm | Tube/Plate | 3 and 10 |
| Schott Glass | | Glass | None | 10 nm and 0.1 μm | Tube | 5–15 |
| Fuji Filters | | Glass Glass | None None | 4–90 nm 0.25–1.2 μm | Tube | |
| Ceram-Filtre | FITAMM | SiC | None | 0.1–8 μm | Monolith | 25 |
| Fairey | Strata-Pore ® Microfiltrex ® | Ceramics SS | Ceramics SS | 1–10 μm 0.2–1 mm | Tube/Plate Tube Plate | 10 |
| Mott | | SS, Ni, Au, Ag, Pt, etc. | None | ≧0.5 μm | Tube | 3.2–19 |
| Pall | | SS, Ni, etc. | None | ≧0.5 μm | Tube | 60 and 64 |
| Osmonics | Hytrex ® Ceratrex ® | Ag Ceramics | None Ceramics | 0.2–5 μm 0.1 μm | Tube/Plate | |
| Ceramem | | Ceramics oxides | Coerdierite | 0.05–0.5 μm | Honeycomb monolith | 1.8 |

Ceramic filters, such as aluminum oxide-based ceramics, provide an improvement over fibrous filters because, inter alia, they biologically inert and resistant to attack by microorganisms; they have higher temperature stability; they can be more readily cleaned, sterilized, and reused; they have a wider chemical compatibility and are more resistant to solvents; and they are mechanically stronger, resist physical compression, and have a longer useful life.

The preferred hydrophobicity or hydrophilicity of the filter material depends upon the type of lipid used to form the liposomes or lipid complexes. For example, for use with liposome and lipid complexes, hydrophilic filters are preferred over filters that are sufficiently hydrophobic such that they cause greater extrusion and/or leakage. Preferably, the filter material is chosen such that the flux rate is not substantially affected by electrostatic interaction between the liposomes or lipid complexes and the filter material.

The filter pores can be tortuous or non-tortuous; branched pore, straight pore or conical pore. See, for example, FIG. 2a in which the pores 30 of the layer 3 of the membrane 27 are straight and FIG. 2b in which the pores 30 of the layer 3 of the membrane 27 are conical pores. Further, the filter pores can be symmetric, with a homogeneous pore structure throughout the membrane, or asymmetric, with a gradual change in pore size throughout the membrane. See, for example, FIGS. 2c and 2d in which the pore size gradually decreases from layer 1 to layer 2 to layer 3. In preferred embodiments, the composite filters have a gradual decrease in pore size to the feed side of the membrane, such as that shown in FIGS. 1a, 2c, 2d, 3d and 4b.

Figure 1A:
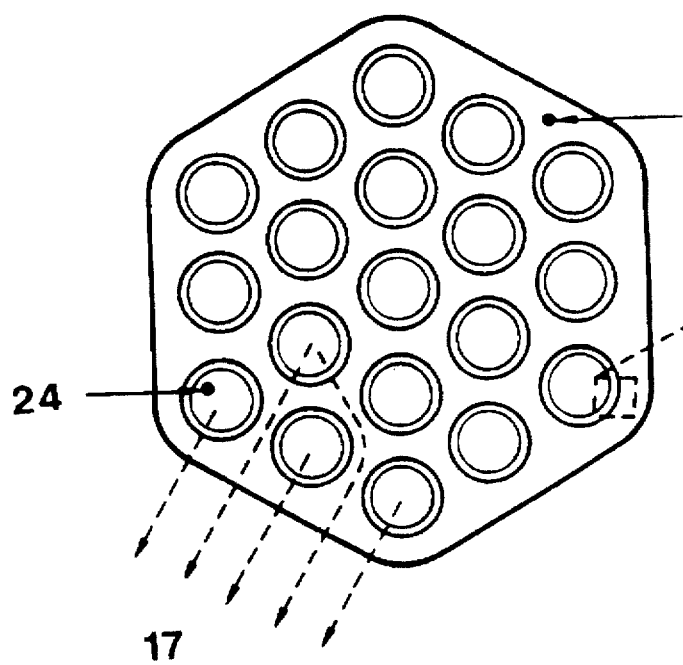
FIG. 1a is a schematic, partial cross-sectional view of the filter shown in FIG. 5, with an enlarged insert to show details of the layers within the filter.
Figures 1, 1A:
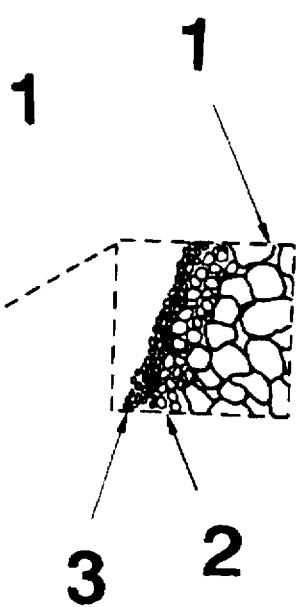
Figure 1B:
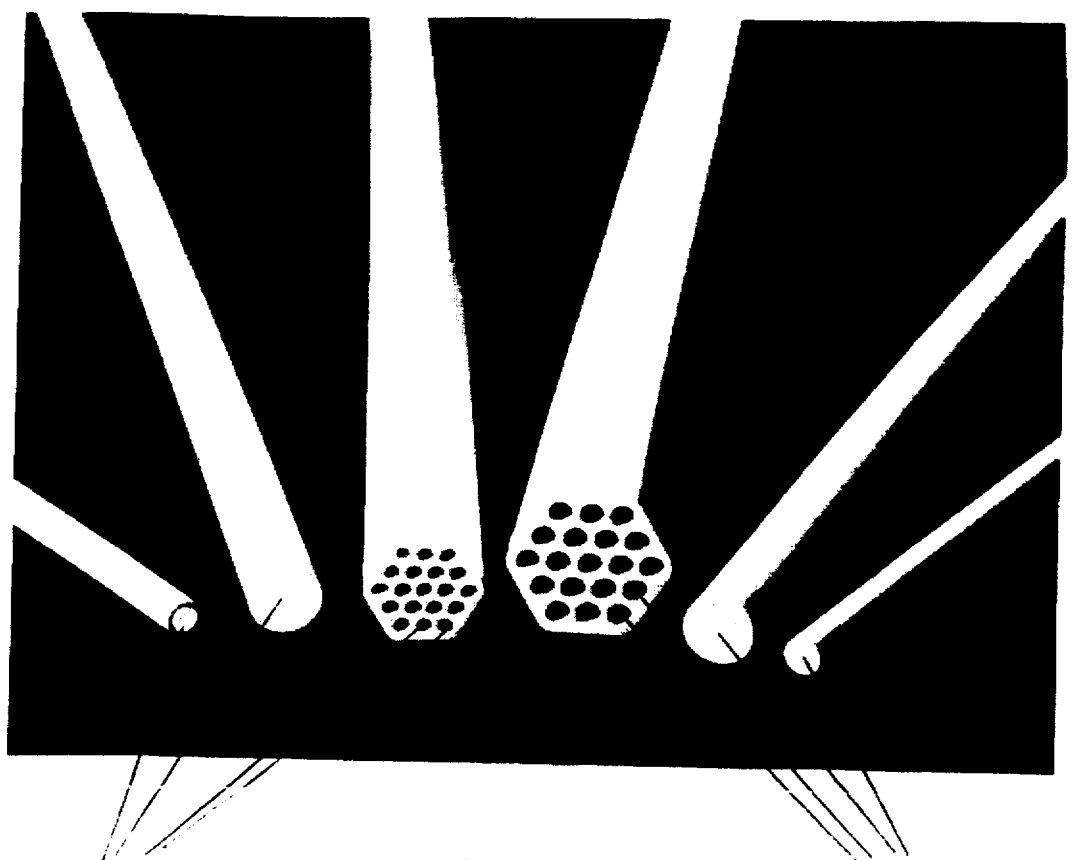
FIG. 1b shows several examples of single-channel and multi-channel tube and honeycomb filter geometry that can be used in accordance with the methods of the present invention. See R. Bhave, *Inorganic Membranes: Synthesis, Characteristics and Applications* (Van Nostrand Reinhold 1991), at page 89, relevant portions of which are hereby incorporated herein by reference.

The structure of the filter can be, for example, multichannel, having more than one channel 24, such as that shown in FIGS. 1a, the two filters in the middle of 1b, 1c, and 5, or a single channel, such as the four filters on each end of FIG. 1b. The geometry of the filter can be, for example, disks, tubes or tube bundles, and multi-channel or honeycomb monoliths, and are preferably multi-channel monoliths. See, for example, FIG. 1b, which illustrates two tubes each on the left and the right, and two multi-channel (honeycomb) monoliths in the middle. Suitable assemblies for containing the filters are, for example, modules containing more than one monolith. See, for example, FIG. 1c, in which there is one monolith in the module in the middle; seven monoliths in the module on the left, and nineteen monoliths in the module on the right.

Separation of the unassociated bioactive agent (for example, a hydrophilic drug) can be accomplished by passing the liquid stream containing the liposomes or lipid complexes through a diafiltration system using uncoated aluminum oxide ceramic filters or fibrous filters. However, such filters do not provide as high flux rates as commercially desirable. Fibrous filters are also disadvantageous because, inter alia, they often become plugged requiring frequent cleaning and/or replacement.

To address these and other problems, the present invention provides methods of separating liposomes or lipid complexes from a fluid comprising passing the fluid through a filter comprising a substrate having a designated pore size and thickness and a membrane thereon having a smaller thickness and nominal pore size than the substrate.

The methods of the present invention can be used, for example, to separate the liposomes or lipid complexes from solvents or from starting materials, such as unassociated bioactive agent. Tangential flow filtration is a preferred embodiment that can be used to separate liposomes or lipid complexes, for example, from solvents or from free (unentrapped or unassociated) bioactive agent in the preparation. In the present invention, the term "tangential flow filtration" is defined as the separation of suspended solids from aqueous or organic fluids or fluid mixture by passing or circulating a sample feed parallel or tangential to the membrane surface, with a filtrate of concentrated solids continuing to flow tangential to the membrane. Preferably, tangential flow filtration is pressure-driven and a fluid is pumped parallel to the filter surface. This tangential flow serves to sweep away retentate and prevent clogging of the filter surface. The pore size of the filter determines which particles will be removed in the filtrate, and those retained in the feed (the "retentate").

For example, a sample feed stock passed through a tangential flow filtration device having a 5.0 µm pore size filter allows passage of particles less than 5.0 µm to pass into the filtrate. Particles larger than 5.0 µm remain in the retentate. The use of filter sizes smaller than the size of the liposomes or lipid complex permits the passage of these smaller solvent or free drug molecules through the filter pores, while retaining the desired product. Thus, extra-liposomal or extra-lipid complex materials can be removed by their ability to pass through the membrane pores, while the liposomes or lipid complexes remain circulating in the retentate. This process can be optionally performed simultaneously with size separation of the liposomes or lipid complexes.

It will also be understood by one skilled in the art, once armed with the present invention, that the methods of the invention may be carried out with multiple filters, with filters of different pore sizes, and with more than one type of filter. For example, the composite filters used in accordance with the methods of the present invention may be combined, for example, with one or more simple filters (non-composite filters in which the membrane and substrate are one in the same). Further, filters used in accordance with the present invention may have different pore sizes. For example, in certain preferred embodiments, a 1.4 µm composite filter, such as a Membralox filter having an aluminum oxide membrane and an aluminum oxide substrate, is used in combination with a 5 µm simple filter, such as a simple aluminum oxide filter, to separate out solvent and size, for example, amphotericin B lipid complexes.

In certain preferred embodiments, such as the filtration of aminoglycosides such as gentamicin, there is no backflushing of the filtrate flow using the methods of the present invention. Backflushing is defined as the application of counterpressure on the filtrate side of the membrane to push a small quantity of filtrate through the substrate into the feed of the module. In other embodiments, such as the filtration of polyene macrolides such as amphotericin B, backflushing is carried out.

The methods of the present invention may be carried out in an open system, a closed system, or a bleed and feed system, as described, for example, in Bhave, *Inorganic Membranes*, at page 144.

Unlike traditional filtration processes, tangential flow filtration prevents a filter cake build-up on the filter surface. Also, there is no "dead-end" extrusion of larger particles due to pressure, as the liquid is caused to flow across a membrane surface. The flow rate of the liquid is therefore maintained as it is passed over the membrane.

As the filtrate is collected from the filter, aqueous or organic solution (for example, sterile buffer or 0.9% NaCl) can be added to the retentate, preferably at the same rate at which filtrate is removed in order to maintain the volume. This process, called diafiltration, enhances the particle yield obtained. In principle, for removal of 90% of a species that can freely pass through the filter (i.e., a zero rejection coefficient wherein virtually none of the species are rejected by the filter), one can maintain the volume of the retentate while washing with buffer, for example, about 2.3 times the volume of the retentate. To remove about 99% of the species, the volume of wash through the filter is preferably about 4.4 to about 4.8, and more preferably about 4.6 times the retentate volume. Diluted filtrate obtained by this diafiltration process can be concentrated later, for example, using tangential flow filtration. Alternatively, a series of dilutions and concentrations can be used to increase the passage of the species of interest into the filtrate. Alternatively, the entire sample can be recirculated through the filter which would not require addition of aqueous solution. Two or more tangential flow filtration devices can be connected in sequence, or in series, in the latter case, preferably with a pump between the units to provide ample flow for the second filtration.

The diafiltration system used to separate liposomes or lipid complexes from the by-products of manufacture can be continuous or discontinuous, and preferably is continuous. In continuous diafiltration systems, water or other solution is added continuously to a feed tank or retentate line at the same rate as the filtrate is removed from the system. Discontinuous diafiltration involves first removing the permeable solutes and then adding water or other solution to the concentrated retentate to dilute the same to the original volume. Further details on the general operation of continuous and discontinuous diafiltration processes can be found in Munir Cheryan, *Ultrafiltration Handbook* (Technomic Publishing Company 1986), pp. 205–213, incorporated herein by reference.

Figure 5A:
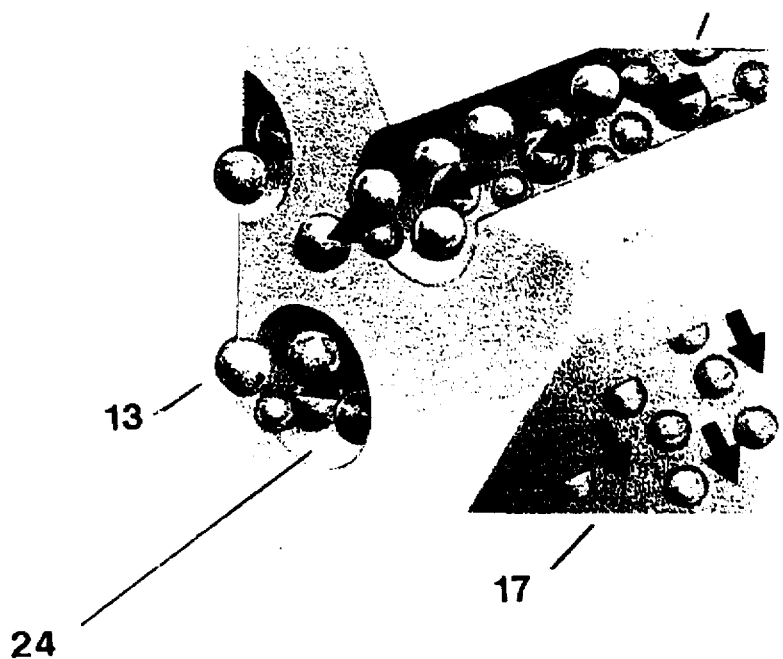
FIG. 5a is a schematic, partial cross-sectional view of an embodiment of a porous filter that can be used in accordance with the methods of the present invention.
Figure 5B:
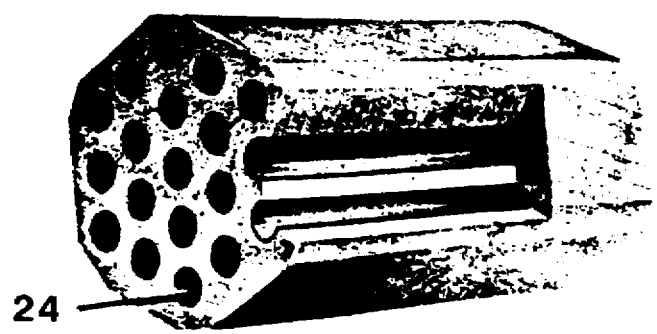
Figure 6:
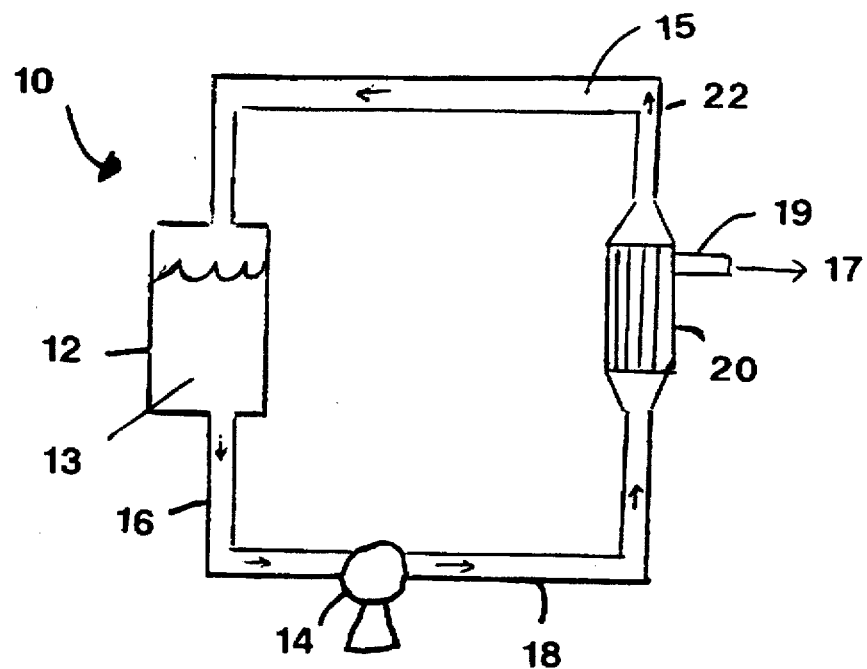
FIG. 6 is a schematic view of an embodiment of a diafiltration system utilizing a tangential flow filter in accordance with the methods of the present invention.
Figure 7:
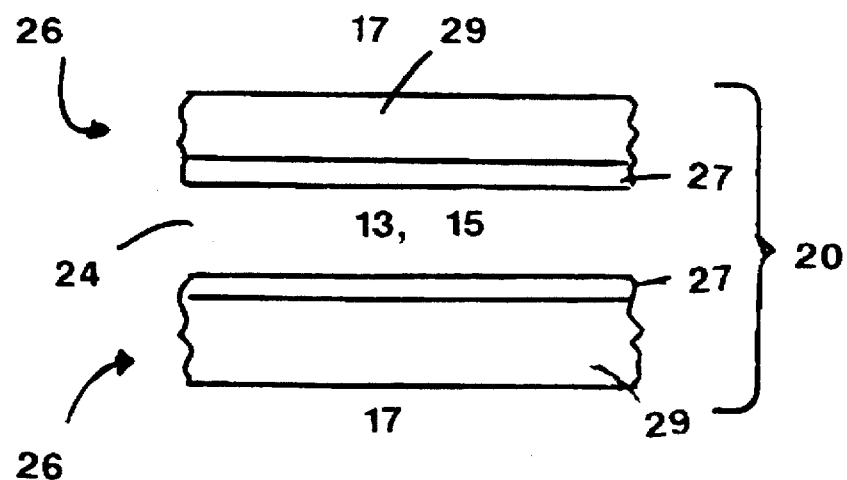
FIG. 7 is a partial cross-sectional view of a tangential flow filter used in the diafiltration system of FIG. 6.

Referring to FIG. 6, there is shown a tangential flow diafiltration system 10 which can be employed in the present invention. The system 10 includes a feed tank 12 which stores the liquid medium containing the material to be separated (the "feed", for example, a mixture containing liposomes or lipid complexes having an associated bioactive agent, unassociated bioactive agent, salts and free lipid). Removal of the feed 13 is controlled by a pump 14 which draws the feed through lines 16 and 18 into a filter assembly 20. Further details of an example of a filter assembly are illustrated in FIGS. 1 and 5, which are discussed below. The filter assembly separates and removes relatively small particles including, for example, water, lipid, salts and unassociated bioactive agent as the filtrate and retains the larger particles (for example, liposomes) as part of the liquid retentate. Referring to FIGS. 5 and 7, the feed stream 13 passes through the channels 24 of the filter. The retentate 15 remains in the channels 24 while the filtrate 17 passes through the filter. Referring to FIGS. 6 and 7, the filtrate 17 is removed via a line 19 while the retentate 15 is removed from the filter assembly 20 via the line 22 and discarded or returned to the feed tank 12.

A cross section of a filter in the filter assembly 20 is shown in an expanded view, for example, in FIG. 7, and includes at least one channel 24 formed by a filter material 26 comprised of a substrate 29 having thereon a membrane 27 which is thinner and has a smaller nominal pore size than the substrate 29. A more detailed schematic view of an example of a filter assembly is shown in FIG. 1, in which the filter has a single membrane layer 3, a bulk substrate layer 1, and an intermediate substrate layer 2. Filtrate 17 passes from the channel 24 through the filter and leaves the filter unit as depicted by the arrows.

In certain preferred embodiments, such as those provided in the examples, the parameters of filtration, preferably using a ceramic membrane, are about a 20 gpm recirculation rate per 2.1 ft$^2$ of ceramic membrane, 20 psi average transmembrane pressure, a local environmental temperature of approximately 22°–28° C., and no backflushing of filtrate flow. Under these optimized conditions, no flux decay was observed for ceramic filters having a ceramic membrane and a ceramic substrate, such as discussed in the examples. Tests showed that backflushing caused a negative effect on filtrate flux, possibly by causing a less desirable surface build-up. Additionally, a preferred target volume ratio was found to be about 3.6 liters of liposomal suspension per square foot of filter area. A larger target volume ratio, such as 19 liters per square foot, was found to increase the amount of time required for diafiltration and induced liposomal damage through shearing. In certain preferred embodiments, about 3 to 3.5 wash volumes are used to separate out, for example, unentrapped bioactive agent. The concentration of the liposomes (as measured by total phospholipid concentration) in certain preferred embodiments, such as when the bioactive agent is gentamicin, is about 40 to about 80 mg/ml. In this concentration range, it was found that, using equivalent amounts of a solution for dilution purposes, the projected diafiltration time is independent of concentration of the liposomes. However, as a general matter, filtrate flux rate decreases as the concentration of the liposomes increases. Preferably, the time required for diafiltration is less than about 8 hours, and more preferably, less than about 4 hours.

The type of materials which can be separated from the liposomes and lipid complexes in accordance with the present invention is unlimited. The liquid feed must contain at least one material which is sufficiently small to pass through the filter as a filtrate. The liposomes or lipid complexes must be sufficiently large to be retained by the filter while small enough to recirculate through the channels of the filter system as the retentate.

The temperature of the local atmosphere during filtration is preferably between about 10° C. to about 40° C., more preferably about 20° C. to about 40° C., even more preferably about 25° C. to about 35° C., and most preferably about 30° C. to about 35° C. Preferably, the temperature is not so high that the liposomes or lipid complexes become damaged, and preferably, the temperature is not so low that the flux rate decreases. One skilled in the art, once armed with the present disclosure, would be able to determine the optimal temperature ranges for a particular composition of liposomes or lipid complexes.

The average transmembrane pressure during filtration is preferably between about 5 and about 100 p.s.i., more preferably about 10 to about 35 p.s.i., even more preferably about 10 to about 30 p.s.i., even more preferably about 15 to about 25 p.s.i., and most preferably about 20 p.s.i. Preferably, the average transmembrane pressure is not so high that the liposomes or lipid complexes are no longer retained by the filter, and not so low that filtration is slow. Average transmembrane pressure is defined as the average pressure difference between the mean internal channel pressure and the pressure of the filtrate leaving the filter. Tests showed that an average transmembrane pressure of 30 psi provided no appreciable increase in flux rate over 20 psi. Therefore, an average transmembrane pressure of 20 psi is preferred for use according to the examples provided in the present invention.

Preferably, the fluid has a recirculation cross-flow velocity of about 3 to about 7 m/sec. Cross-flow velocity is defined as the average rate at which the process fluid flows parallel to the membrane surface.

The liposomes to be separated according to the present invention may be prepared in a variety of ways. They include Bangham's method of making multilamellar vesicles (MLVs). See 13 *J. Mol. Biol.* 238 (1965), the contents of which are incorporated herein by reference. This method involves first forming a solution of lipids in an organic solvent and then evaporating the solvent, leaving a thin lipid film on the interior surface of the reaction vessel to which an aqueous solution is added. Hydration of the lipid film results in the formation of MLVs.

Large unilamellar vesicles (LUVs) can be made by extruding MLVs, under pressure, through filters, according to the procedure disclosed by Cullis et al. (U.S. Pat. No. 5,008,050, the contents of which are incorporated herein by reference). Alternatively, LUVs can be formed by infusion, reverse-phase evaporation or detergent dilution techniques. See, e.g., Deamer and Uster, "Liposome Preparation: Methods and Materials," in: *Liposomes*, Marcel Dekker, Inc., New York (1983), pp. 27–51, the contents of which are incorporated herein by reference.

Multilamellar vesicles can have substantially equal interlamellar solute distribution. Their preparation is described in Lenk et al., U.S. Pat. Nos. 4,522,803 and 5,030,453, and Fountain et al., U.S. Pat. No. 4,588,708, the contents of these being incorporated by reference herein. The Lenk et al. process involves mixing an aqueous solution of the solute to be entrapped with an organic solution of the lipid(s) being used. Fountain's process involves first forming an organic solution of a lipid and an aqueous component in an amount sufficient to form a monophase. The organic solvent is then evaporated and a second aqueous component is added, with agitation, to form the liposomes.

The methods of the present invention can be carried out with liposomes or lipid complexes made of any types of materials, including, but not limited to, phospholipids, such as phosphatidylcholine, phosphatidylethanolamine, lysophosphatidylcholine, lysophosphatidylethanolamine, phosphatidylserine, phosphatidylinositol, phosphatidic acid, dimyristoylphosphatidylglycerol and diphosphatidylglycerol; synthetic saturated compounds, such as dimyristoylphosphatidylcholine, dipalmitoylphosphatidylcholine, and distearoylphosphatidylcholine; and unsaturated species such as dioleoylphosphatidylcholine or dilinoleoylphosphatidylcholine. Further, a variety of cholesterols and other sterols and their water soluble derivatives can be used to form liposomes in conjunction with other lipids; see Janoff et al., U.S. Pat. Nos. 4,891,208 and 5,041,278, each incorporated herein by reference.

Hydrophilic bioactive agents can be entrapped in liposomes by dissolving the bioactive agent in the aqueous medium to which lipids are added. A portion of the drug will be encapsulated in the resulting liposomes as they are formed. Alternatively, the liposomes can first be prepared and then loaded with ionizable bioactive agents by establishing a potential difference across the liposomal bilayer.

See Bally et al., U.S. Pat. No. 5,077,056, the contents of which are incorporated herein by reference. Hydrophobic bioactive agents can be entrapped in the bilayers of liposomes by adding the bioactive agents to solutions of the lipids from which the liposomes are formed.

The methods of this invention can be practiced using liposomes synthesized by any of the above-described preparatory and loading techniques, or any other methods for making liposomes and loading them with bioactive agents which are now known or later developed. "Bioactive agent", as the term is used herein, means a chemical compound, whether natural or synthetic, that exhibits biological activity.

In certain preferred embodiments, the present process is used for separation following the preparation of liposomes having a hydrophilic bioactive agent associated therewith, such as aminoglycosides, including gentamicin ($C_1$, $C_{1a}$ and $C_2$), streptomycin, dihydrostreptomycin, tobramycin, neomycin B, paromycin, ribostamycin, lividomycin, kanamycin A and B, viomycin, sisomicin, netilimicin and amikacin, as well as analogues and derivatives thereof. In certain preferred embodiments, the methods of the present invention are used to separate unassociated gentamicin.

Other bioactive agents include but are not limited to antibacterial compounds such as the aminoglycosides; antiviral compounds, such as rifampacin or azidothymidine (AZT); antiparasitic compounds, such as antimony derivatives; antineoplastic compounds, such as vinblastine, vincristine, mitomycin C, doxorubicin, daunorubicin, methotrexate, and cisplatinum, among others; proteins such as albumin; toxins, such as diptheria toxin; enzymes, such as catalase; hormones, such as estrogens; neurotransmitters, such as acetylcholine, lipoproteins, such as alpha-lipoprotein; glycoproteins, such as hyaluronic acid; immunoglobulins, such as IgG; immunomodulators, such as the interferons or the interleukins; dyes, such as Arsenazo III; radiolabeled compounds, such as $^{14}C$; radio-opaque compounds, such as $^{99}Te$; fluorescent compounds, such as carboxy fluorescein; polysaccharides, such as glycogen; cell receptor binding molecules, such as estrogen receptor protein; nonsteroidal anti-inflammatories, such as indomethacin, salicylic acid acetate, ibuprofen, sulindac, piroxicam, and naproxen; anti-inflammatories, such as dexamethasone; antiglaucomic agents, such as timolol or pilocarpine; anesthetics, such as dibucaine; nucleic acids, such as thymine; polynucleotides, such as RNA polymers; cardiovascular agents, such as alpha-blocker, beta-blocker, calcium channel blockers, ACE inhibitors, and the like; CNS agents; prostaglandins; neurotransmitters; glycoproteins; immunoglobulins; immunomodulators; polysaccharides; antiglaucomic agents; mydriatic compounds; and the like. Specific examples of such bioactive agents and their incorporation into liposomes can be found in Lenk et al., U.S. Pat. No. 4,522,803; Fountain et al., U.S. Pat. No. 4,588,578; Janoff et al., U.S. Pat. Nos. 4,861,580 and 4,897,384; and Lenk et al., U.S. Pat. No. 5,082,664; each of which is incorporated herein by reference.

One method of preparation of liposomes wherein the associated bioactive agent is a hydrophilic bioactive agent involves adding the bioactive agent to the aqueous phase. The lipid and an organic solvent are combined to form a solution which is added to the aqueous phase, thus forming liposomes. The aqueous phase can, for example, be a solution of one or more drying protectants such as a saccharide (e.g. maltose) or polyhydric alcohol (e.g. mannitol) with or without a preservative (e.g. disodium EDTA).

In certain preferred embodiments, the methods of the present invention are used to separate out lipid complexes from, for example, a solvent. Lipid complexes are also known as non-liposomal high drug:lipid ratio complexes (HDLCs). Lipid complexes can be formed by liposome-forming procedures using high drug:lipid ratios. Lipid complexes may be made according to the processes described in WO 88/06443 (Janoff et al., Sep. 7, 1988), U.S. Pat. No. 5,100,591 (Leclef et al.) and U.S. Pat. No. 4,973,465 (Baurain et al.), relevant portions of each of these documents being incorporated herein by reference. A drug:lipid ratio that forms HDLCs is between about 6 and about 50 mole percent hydrophobic drug, preferably between about 15 and about 50, more preferably between about 25 to about 50, and even more preferably between about 25 to about 45 mole percent. Between about 6 and about 25 mole percent hydrophobic drug, a mixed population of liposomes and lipid complexes is formed. Within this range, as the mole percent of drug approaches 25, a greater percent of the structures are complexes rather than liposomes. Complexes are characterized, for example, by freeze-fracture electron micrographs, captured volume measurements that demonstrate essentially zero entrapped volumes, differential scanning calorimetry showing no lipid bilayer pre-transition phase or main transition, $^{31}P$-NMR spectra that suggest characteristics of highly immobilized lipid (broad isotropic), x-ray diffraction data indicative of gel phase lipid, and density gradient centrifugation followed by elution to show complete association of the drug with the lipid.

In certain preferred embodiments, the methods of the present invention are used to separate lipid complexes having a polyene macrolide antibiotic compound from a solvent, and in preferred embodiments, the lipid complexes are sized at the same time. Examples of polyene macrolide antibiotics include but are not limited to amphotericin B, nystatin, pimaricin, candicidin, and filipin.

The liposomes and lipid complexes that are formed by the above-described processes typically vary over a wide range of particle sizes. It is often desirable to produce a more uniform population distribution encompassing a desired mean particle size. The term "mean particle size" shall mean the sum of the diameters of each liposome or lipid complex divided by the total number of liposomes or lipid complexes.

If desired, the liposome population can be size-reduced to a more uniform population distribution, for example, by extrusion through a 100 nm filter as described in Cullis et al. U.S. Pat. No. 5,008,050 or an Anopore filter as described in Coe et al. WO 92/05772 (Apr. 16, 1992). Liposomes of about 100–200 nm are generally obtained using this method. The resulting size reduced liposome product can be sterilized, for example, by passage through a 200 nm sterilizing filter.

The liposome population can be passed through a filter having a pore size generally corresponding to the desired mean particle size. Each passage of the liposomes through the filter reduces the size of some of the larger liposomes to a size more closely resembling the desired mean particle size. After several passes through the filter, the resulting liquid medium contains a more uniform population distribution of the liposomes as well as unassociated (free) bioactive agent (if present) and free lipid material.

The application of an aluminum oxide porous film to the size reduction of liposomes to obtain a more uniform population distribution is disclosed in Royden M. Coe et al., WO 92/05772 (Apr. 16, 1992), incorporated herein by reference. The separation methods of the present invention can be used to size liposomes or lipid complexes.

Homogenization is another method for size reducing liposomes. In a simple homogenization method, a suspension of liposomes is repeatedly pumped under high pressure through a small orifice or reaction chamber until a desired population distribution is achieved.

The methods of the invention are illustrated by the examples below, which are not intended to limit the invention in any way.

EXAMPLE 1

An experimental study was conducted to compare various types of filters for extraneous solute removal for filtration of liposomal gentamicin.

The following filters were tested: Ceramic filters (Millipore Corp. (Bedford, Mass.) and IWT (Rockford, Ill.; subsidiary of U.S. Filter), suppliers), Enka (hydrophobic) polypropylene hollow fiber filter cartridges (Microdyn Technologies, Inc., Raleigh, N.C., importer), Prostak filter cartridges (tangential flow filter systems with several membrane materials; Millipore Corp.), and Membrex (Membrex Corp., Fairfield, N.J.) rotary tangential flow filtration, which incorporates high speed rotation of the filter to improve mixing within the filter housing.

For each type of filtration system, a variety of nominal pore sizes and, where applicable, several membrane materials were examined. Where appropriate, both hydrophilic and hydrophobic membrane materials were tested.

The liposomal suspensions tested had gentamicin associated therewith as well as unassociated free gentamicin. The concentration of gentamicin used in these experiments was approximately 25 mg/ml, and the liposome particle size ranged from less than about 1 µm to about 12 µm. The liposomal formulation was prepared by the emulsification process disclosed in Lenk et al., U.S. Pat. No. 4,522,803, and primarily contains liposome associated gentamicin (prepared from egg phosphatidylcholine and methylene chloride), free gentamicin, free lipid, salts, and water. Five and one-half liters of undiafiltered liposomal gentamicin was used in the "Preliminary Test". Twelve liters of undiafiltered liposomal gentamicin comprised of two essentially equivalent batches was used in the "Main Test". Previously diafiltered liposomal gentamicin was used in the "Comparative Test". In the tables of test results (Tables 2–6), the row "test material used" refers to which pool of liposomal gentamicin was used in each test.

TABLE 2

MICROGON AND ENKA HOLLOW FIBER FILTER TEST RESULTS

| Test No. | MICROGON TESTS | | | | ENKA TEST |
|---|---|---|---|---|---|
| | 1 | 2 | 3 | 4 | 5 |
| Filter Type | Hollow Fiber Cartridge | Hollow Fiber Cartridge | Hollow Fiber Cartridge | Hollow Fiber Cartridge | Hollow Fiber Cartridge |
| Nominal Pore Size | 0.2 µm | 0.2 µm | 0.2 µm | 0.2 µm | 0.2 µm |
| Mat'l of Construction | Cellulose Acetate/ nitrate | Cellulose Acetate/ nitrate | Cellulose Acetate/ nitrate | Cellulose Acetate/ nitrate | polypropylene |
| Hydrophilic/Hydrophobic | Hydrophilic | Hydrophilic | Hrdrophilic | Hrdrophilic | Hydrophobic |
| Surface Area of Filter | 1.0 ft$^2$ | 1.0 ft$^2$ | 1.0 ft$^2$ | 1.0 ft$^2$ | 0.43 ft$^2$ |
| Test Mat'l Used | Main Test | Preliminary Test | Comparative Test | Comparative Test | Main Test |
| Test Volume Ratio (L/ft$^2$) | 1.37 l/ft$^2$ | 1.06 l/ft$^2$ | 0.44 l/ft$^2$ | 0.44 l/ft$^2$ | 0.47 l/ft$^2$ |
| System Recirc. Rate | 2.8 gpm | 2.0 gpm | 3.0 gpm | 6.0–6.5 gpm | 0.08 gpm |
| Mean Internal Lumen Pressure/ Mean Transmembrane Pressure | 8 psi/8 psi | 6.3 psi/6.3 psi | 2 psi/2 psi | 18 psi/18 psi | N/D |
| Flux Rate (ml/min ft$^2$) | 14.6 → 4.8 | 14.6 → 7.5 | 20 ml/min ft$^{2(1)}$ | 12.5 → 6.0 | 13–17 ml/min ft$^2$ |
| Lipid Leakage | | | | | |
| Clear/Cloudy? | Clear | Clear | Clear | Clear | Clear |
| Filtrate Assay (lipid) | 0.015 mg/ml | 0.004 mg/ml | 0.004 mg/ml | 0.028 mg/ml | 0.11, 0.23 mg/ml |
| Est. % Lipid in Retentate Lost (calc. from Filtrate Assay) | 0.10% | 0.028% | one wash only | one wash only | 1.36% |
| Actual % Lipid Lost$^{(2)}$ | 16.8% | <0.1% | | | 12.4% |

$^{(1)}$one wash only $^{(2)}$Calculated as $1 - \frac{\text{mg/ml lipid in final retentate}}{\text{mg/ml lipid in baseline mat'l}}$ Subject to errors due to uncertainties in measurement of total volume

TABLE 3

CERAMIC FILTER TEST RESULTS

| Test No. | 6 | 7 | 8 | 9 |
|---|---|---|---|---|
| Filter Type | Multi-Lumen Ceramic | Multi-Lumen Ceramic | Multi-Lumen Ceramic | Single-Lumen Ceramic |
| Nominal Pore Size | 0.2 µm | 0.45 µm (2 washes/ 0.2 µm (5 washes) | 1.0 µm | 0.45 µm |
| Mat'l of Construction | Ceramic | Ceramic | Ceramic | Ceramic |
| Hydrophilic/Hydrophobic | Hydrophilic | Hydrophilic | Hydrophilic | Hydrophilic |
| Surface Area of Filter | 0.4 ft$^2$ | 0.4 ft$^2$ | 0.4 ft$^2$ | 0.06 ft$^2$ |
| Test Mat'l Used | Main Test | Main Test | Main Test | Preliminary Test |
| Test Volume Ratio (L/ft$^2$) | 3.0 l/ft$^2$ | 2.5 l/ft$^2$ | 1.5 l/ft$^2$ | 17.7 l/ft$^2$ |
| System Recirc. Rate | 5.5 gpm | 5.0–6.0 gpm | 5.0 gpm | 3.6 gpm |

TABLE 3-continued

CERAMIC FILTER TEST RESULTS

| Test No. | 6 | 7 | 8 | 9 |
|---|---|---|---|---|
| Mean Internal Lumen Pressure/ Mean Transmembrane Pressure | 8 psi/8 psi | 6–7 psi/-.7 psi | 6 psi/6 psi | 6.3 psi/6.3 psi |
| Flux Rate (ml/min ft$^2$) | 17–21.5 ml/min ft$^2$ | 18–25 ml/min ft$^2$ | N/A | N/A |
| Lipid Leakage | | | | |
| Clear/Cloudy? | Slightly Cloudy | 0.45 μm-cloudy 0.2 μm clear | severe leakage | Clear |
| Filtrate Assay (lipid) | 0.052–0.280 mg/ml | 0.45 μ-10.1 mg/ml 0.2 μm-<0.02 mg/ml | test discontinued N/A | 0.017 mg/ml |
| Est. % Lipid in Retentate Lost (calc. from Filtrate Assay) | 6.7% | 20.7% | one wash only | one wash only |
| Actual % Lipid Lost[2] | 3.4% | 42.6% | | |

TABLE 4

PROSTAK FILTER TEST RESULTS

| Test No. | 10 | 11 |
|---|---|---|
| Filter Type | Millipore Prostak Cartridge | Millipore Prostak Cartridge |
| Nominal Pore Size | 0.1 μm | 200K MWCO |
| Mat'l of Construction | Durapore (PVDF, coated) | PVDF |
| Hydrophilic/Hydrophobic | Hydrophilic | Hydrophobic |
| Surface Area of Filter | 2.0 ft$^2$ | 2.0 ft$^2$ |
| Test Mat'l Used | Main Test | Main Test |
| Test Volume Ratio (L/ft$^2$) | 0.75 l/ft$^2$ | 0.75 l/ft$^2$ |
| System Recirc. Rate | 5.5–6.0 gpm | 5.5–6.0 gpm |
| Mean Internal Lumen Pressure/ Mean Transmembrane Pressure | 11 psi/11 psi[1] 15 psi/15 psi[2] | 6 psi/6 psi 15 psi/15 psi[3] |
| Flux Rate (ml/min ft$^2$) | 10–12 ml/min ft$^2$ | 11–13 ml/min ft$^2$ |
| Lipid Leakage | | |
| Clear/Cloudy? | cloudy-quit after 3rd wash | Clear |
| Filtrate Assay | 0.51 mg/ml[1], 3.35 mg/ml[2] | <0.02 mg/ml |
| Est. % Lipid in Retentate Lost (calc. from Filtrate Assay) | 5.9% (in 3 washes) | <0.14% |
| Actual % Lipid Lost | 7.6% (in 3 washes) | 10.4% |

[1] lower pressure data
[2] higher pressure data
[3] different pressures appear no to effect flux or lipid leakage

TABLE 5

VARIOUS MEMBREX FILTER TEST RESULTS

| Test No. | 12 | 13 | 14 | 15 | 16 | 17 |
|---|---|---|---|---|---|---|
| Filter Type | Membrex Cartridge | Membrex Cartridge | Membrex Cartridge | Membrex Cartridge | Membrex Cartridge | Membrex Cartridge |
| Nominal Pore Size | 0.1 μm | 0.2 μm | 0.2 μm | 0.1 μm | 100K MWCO (Brand new) | 100K MWCO (used) |
| Mat'l of Construction | Polysulfone | Polysulfone | Polysulfone | Stainless Steel | Polyacrylonitrile | Polyacrylonitrile |
| Hydrophilic/Hydrophobic | Hydrophilic | Hydrophilic | Hydrophilic | N/A | Hydrophilic | Hydrophilic |
| Surface Area of Filter (ft$^2$) | 0.215 | 0.215 | 0.215 | 0.215 | 0.215 | 0.215 |
| Rotational Speed | 2000 RPM | 2000 RPM | 2000 RPM | 2000 RPM | 2000 RPM | 2000 RPM |
| Test Mat'l Used | Main Test | Preliminary Test | Main Test | Preliminary Test | Preliminary Test | Preliminary Test |
| Test Volume Ratio (l/ft$^2$) | 0.86 | 0.93 | 0.86 | 0.93 | 0.47 | 1.86 |
| System Recirc. Rate | 0.079 gpm | 0.079 gpm | 0.079 gpm | 0.079 gpm | 0.079 gpm | 0.079 gpm |
| Mean Internal Lumen Pressure/ Mean Transmembrane Pressure | 2–4 psi/2–4 psi | 2–4 psi/2–4 psi | 2–4 psi/2–4 psi | 2–4 psi/2–4 psi | 8–12 psi/8–12 psi | 20 psi/20 psi |
| Flux Rate (ml/min ft$^2$) | 33.7–37.7 | 32.6–16.3 | N/A | N/A | 20.5 | 13.3 |

TABLE 5-continued

VARIOUS MEMBREX FILTER TEST RESULTS

| Test No. | 12 | 13 | 14 | 15 | 16 | 17 |
|---|---|---|---|---|---|---|
| | | (decreased over time) | | | | |
| Lipid Leakage | | | | | | |
| Clear/Cloudy? | Clear | Slightly Cloudy | Cloudy | Milky | Milky | Milky |
| Filtrate Assay (lipid) | 0.029 mg/ml | N/A | 1.41 mg/ml | leaks profusely | 7.55, 6.14 mg/ml | 7.79 mg/ml |
| Est. % Lipid in Retentate Lost (calc. from Filtrate Assay) | 0.196% | <1.0% | test discontinued | test discontinued | test discontinued | test discontinued |
| Actual % Lipid Lost | 5.7% | <1.0% | | | 19.1% | |

TABLE 6

MEMBREX TEFLON FILTER TEST RESULTS

| Test No. | 18 | 19 | 20 | 21 | 22 | 23 |
|---|---|---|---|---|---|---|
| Filter No. | Pilot Scale Membrex Cartridge | Membrex Cartridge | Membrex Cartridge | Membrex Cartridge | Membrex Cartridge | Membrex Cartridge |
| Nominal Pore Size | 0.2 μm | 0.2 μm | 0.2 μm | 0.2 μm | 0.2 μm | 0.2 μm |
| Mat'l of Construction | Teflon | Teflon | Teflon | Teflon | Teflon | Teflon |
| Wetting Agent | Isopropanol | None | None | Ethanol/water | Ethanol/water | Ethanol/water |
| Hydrophilic/Hydrophobic | Hydrophobic | Hydrophobic | Hydrophobic | Hydrophobic | Hydrophobic | Hydrophobic |
| Surface Area of Filter (ft$^2$) | 2.69 | 0.215 | 0.215 | 0.215 | 0.215 | 0.215 |
| Rotational Speed | 1500 RPM | 2000 RPM | 2000 RPM | 2000 RPM | 2000 RPM | 2000 RPM |
| Test Mat'l Used | Main Test | Main Test | Preliminary Test | Preliminary Test | Comparative Test | Comparative Test |
| Test Volume Ratio (l/ft$^2$) | 0.74 | 0.86 | 0.93 | 0.47 | 0.47 | 0.71 |
| System Recirc. Rate | 0.26 gpm | 0.079 gpm | 0.079 gpm | 0.079 gpm | 0.079 gpm | 0.079 gpm |
| Mean Internal Lumen Pressure/ Mean Transmembrane Pressure | 4.0 psi/4.0 psi | 2–4 psi/2–4 psi | 2–4 psi/2–4 psi | 2–4 psi/2–4 psi | 2–4 psi/2–4 psi | 2–4 psi/2–4 psi |
| Flux Rate (ml/min ft$^2$) | 40–48 | N/A | 27.9–34.9 | 41.9–55.8 | 41.9–74.4 | 51.2–53.5 |
| Lipid Leakage | | | | | | |
| Clear/Cloudy? | Cloudy | Cloudy | Slightly Cloudy | Slightly Cloudy | Slightly Cloudy | Slightly Cloudy |
| Filtrate Assay (mg/ml) | 6.4–15.0 | 3.37–3.98 | 0.445[(1)]–0.060 | 0.602 mg/ml | 0.29–0.51 | 1.60[(1)]–0.549 |
| Est. % Lipid in Retentate Lost (calc. from Filtrate Assay) | 17.8–41.7% | test discontinued | 1.76% | test discontinued | 3.1% | 8.5% |
| Actual % Lipid Lost | 40.3% | | 6.5% | | 8.8% | 14.1% |

[(1)]1st wash filtrate assay value

Diafiltration tests consisted of seven saline washes for a total of 4.6 times the volume of liposomal gentamicin being diafiltered. A recirculating diafiltration system was used for all experiments; the material being diafiltered was pumped in a recirculating loop through the filter being tested. See, for example, FIG. 6. For each wash, the saline wash volume was added to this bulk volume, and then filtrate of an equal volume was removed.

For most of the tests, a hopper and a Millipore Prostak mammalian cell system pump unit together with the filter being tested comprised the diafiltration system. The Prostak unit includes two large capacity 701U/R Watson-Marlow pumps and three pressure transducers which allow for easy pressure read-out. A recirculating cooling bath was used to maintain the liposomal gentamicin temperature in the range 20°–25° C. for all tests. Due to the limited capacity of the filter, the Enka filter test was conducted using a bench scale set-up including a Masterflex model 7562-00 pump. The Membrex tests were performed using the Membrex Benchmark laboratory scale system, with the exception of Test No. 18 (Table 6), which was run using the Membrex Pacesetter pilot scale system.

For each diafiltration experiment, samples of the following were collected for assays: baseline material prior to diafiltration, final retentate at the end of diafiltration, and filtrates (first wash, second wash and seventh wash). In some cases, additional samples were collected. All samples were at least 7 ml in volume. Care was taken to thoroughly mix all liposomal gentamicin and filtrates prior to sampling.

Figure 8:
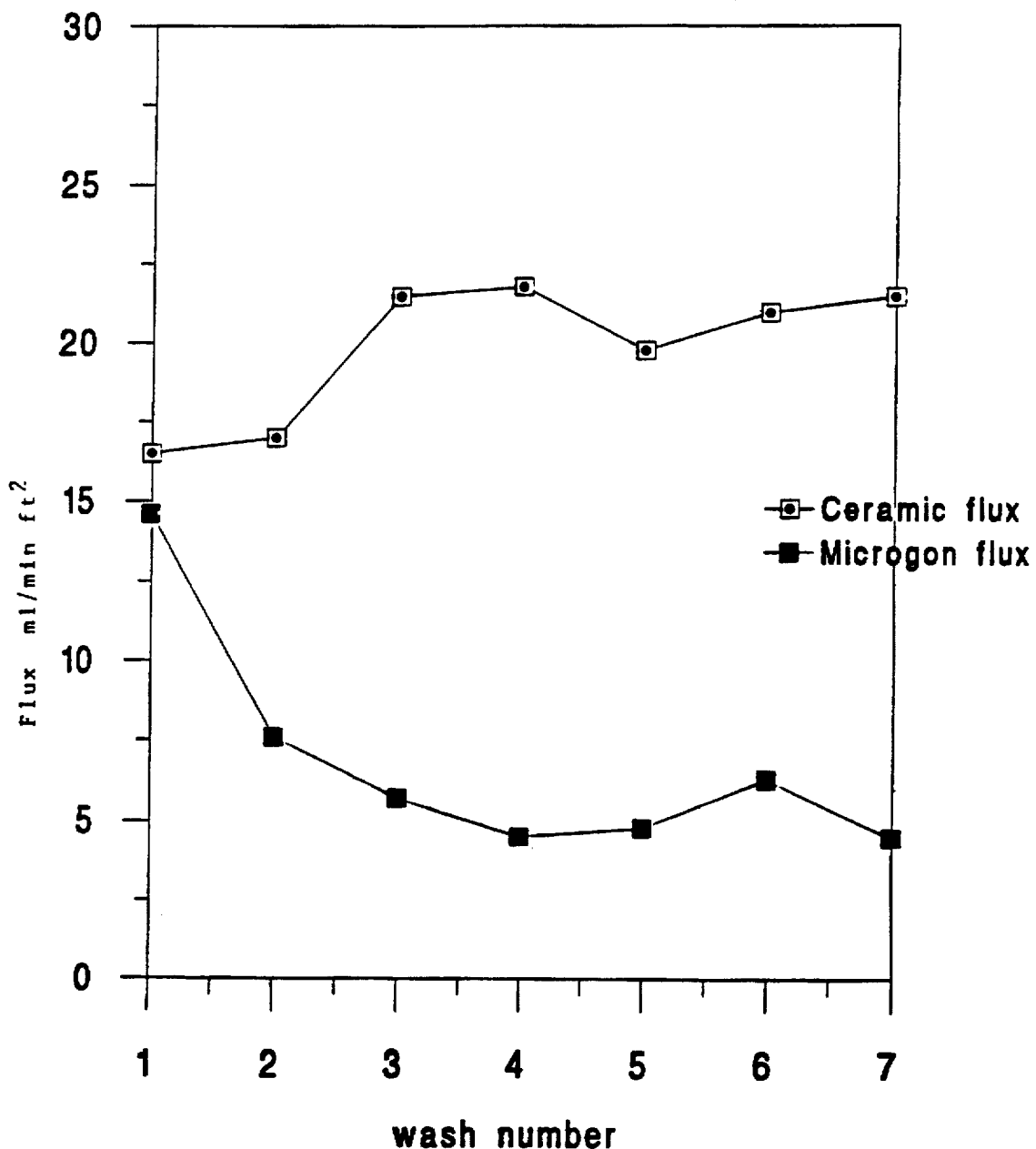
FIG. 8 is a graph that depicts a comparison of ceramic and Microgon (fibrous) filter flux rates through seven washes during a diafiltration run.

A comparison of the flux rates of a ceramic filter versus a fibrous filter (Microgon's cellulose acetate/cellulose nitrate membrane) showed that the ceramic filter maintained a higher and more stable flux rate over seven washes of a diafiltration run. See FIG. 8, which graphically demonstrates the flux rate.

Diafiltration of liposomal gentamicin is a demanding application for all the filters evaluated in this study. Although diafiltration can still be accomplished, flux rates are substantially lower (approximately an order of magnitude lower) than the manufacturers would expect. It appears that there is a rapid non-specific surface binding of some lipid component(s) of liposomal gentamicin to certain filter surfaces that substantially inhibits their effectiveness. This behavior differs from the build-up of a polarized or gel of product on the membrane due to its immediacy when liposomal gentamicin contacts the membrane.

Since a variety of membrane materials was tested, the use of hydrophobic membrane materials for liposomal gentamicin diafiltration was compared to hydrophilic membrane materials under similar test conditions. Direct comparison was made for two sets of experiments (all 0.2 µm nominal pore size): The Enka polypropylene hollow fiber filter versus the Microgon mixed cellulosic hollow fiber filter, and the Membrex teflon filter versus the Membrex polysulfone filter (Tables 2, 5, and 6). Comparing the data from these sets of experiments suggests that hydrophobic filters, properly wetted, provide higher flux rates than hydrophilic filters for liposomal gentamicin diafiltration under similar test conditions. However, all other factors again held equal, hydrophobic filter materials appear to allow higher levels of liposomal leakage. In addition, for the microfilters examined in this study, except for the very hydrophilic Microgon filters, higher pressure operation appears related to increased liposomal leakage across the filter.

In addition, the results of this study suggest that particular caution should be applied when considering use of ultrafiltration membranes for liposomal gentamicin diafiltration. The experiments performed using the Membrex polyacrylonitrile ultrafiltration membranes suggest that liposomal gentamicin liposomes can be extruded/damaged in some filtration processes. Higher filtration pressures coupled with small pore size filter materials and chemical interactions, such as the material's hydrophobicity or hydrophilicity, likely contribute to the resulting large amounts of lipid extrusion.

EXAMPLE 2

A diafiltration system of the type illustrated in FIG. 6 was used to separate liposomes having gentamicin associated therewith from unassociated free gentamicin. The liposomal formulation was prepared by the emulsification process disclosed in Lenk et al., U.S. Pat. No. 4,522,803, and primarily contains liposome associated gentamicin (prepared from egg phosphatidylcholine and methylene chloride), free gentamicin, free lipid, salts, and water.

Figure 1C:
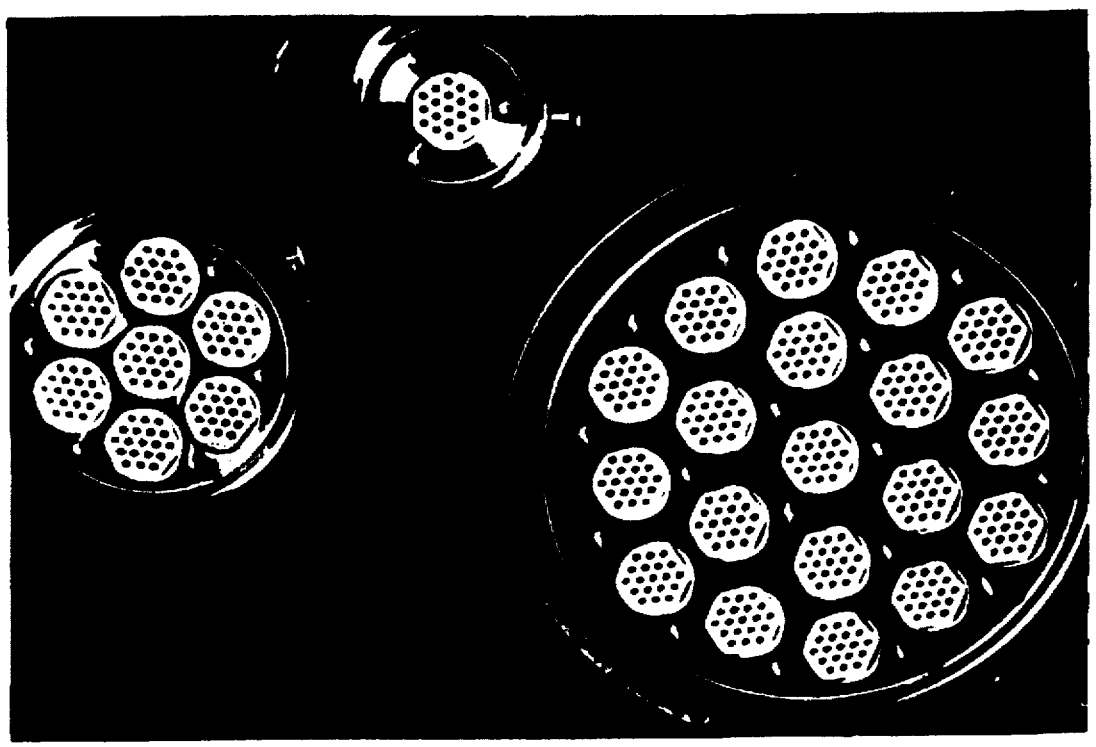
FIG. 1c illustrates three embodiments of filter assemblies that can be used in accordance with the methods of the present invention. The left side illustrates an assembly containing 7 multi-channel filters; the middle shows an assembly with a single multi-channel filter; and the right side shows an assembly with 19 multi-channel filters.
Figure 2A:
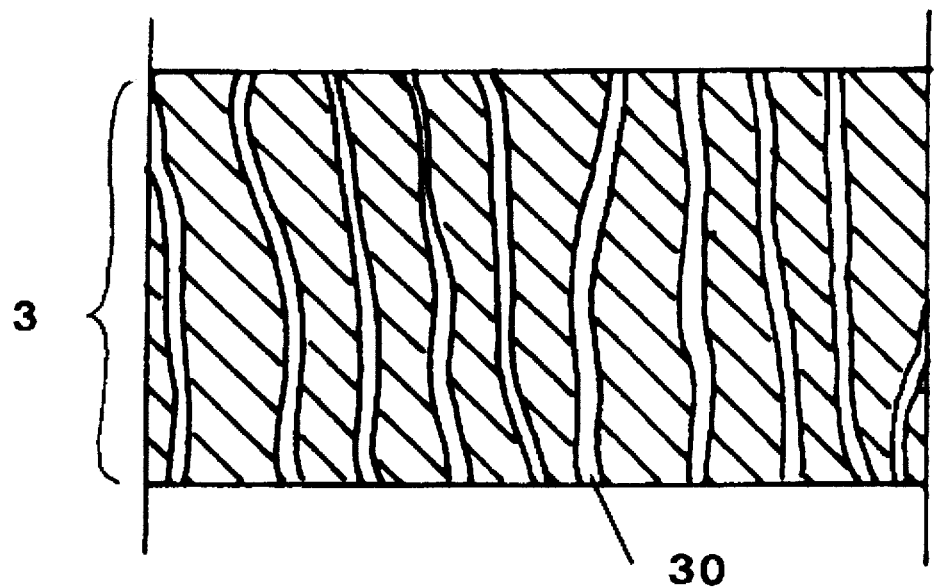
FIG. 2a is a schematic representation of homogeneous straight pores.
Figure 2B:
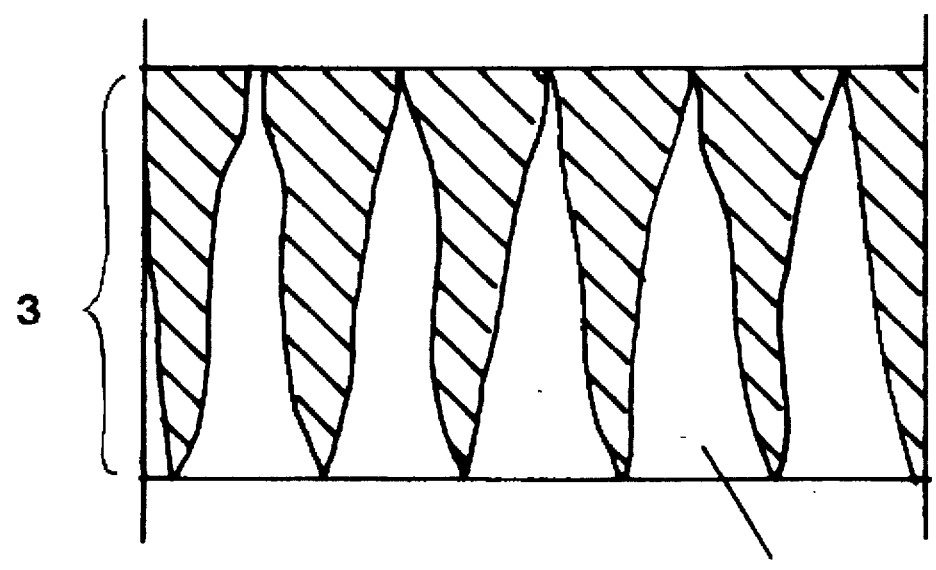
FIG. 2b is a schematic representation of homogeneous conical pores.
Figure 3A:
FIG. 3a is a schematic representation of a modification of pores in a membrane wherein there are homogeneous layers in the pores.
Figure 3B:
FIG. 3b is a schematic representation of a modification of pores in a membrane wherein there are partial plugs in the pores.
Figure 3C:
FIG. 3c is a schematic representation of a modification of pores in a membrane wherein there is/are layer(s) or partial plugs (4) on top of the pores. See Bhave, *Inorganic Membranes*, at page 14.
Figure 3D:
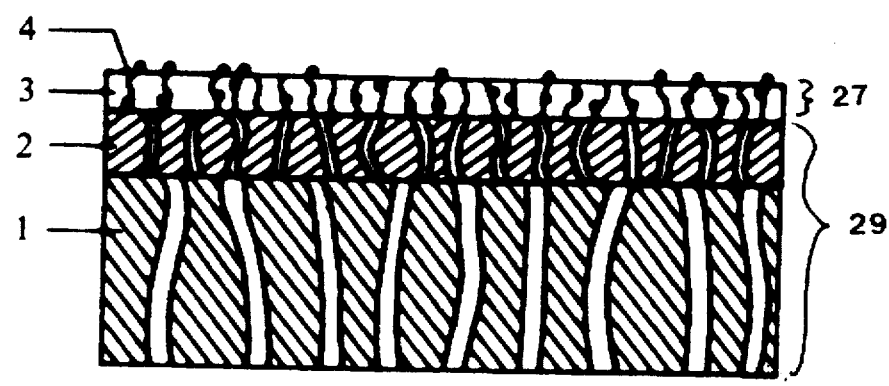
FIG. 3d is a schematic representation of an asymmetric composite filter having: (1) a porous substrate layer with 1–15 µm pores (2), an intermediate substrate layer with 0.1–1.5 µm pores, (3) a membrane with 0.003–0.1 µm pores, and (4) a modification of the membrane. See Bhave, *Inorganic Membranes*, at page 13.

Four ceramic filters, each installed in a filter assembly similar to the assembly shown in FIG. 1c, on the right, were tested one at a time. Two of the filters were composed of an aluminum oxide substrate coated with a 0.4 mm layer of aluminum oxide, such as that shown in FIG. 4a. The remaining two filters were composed of the same aluminum oxide substrate coated with a 0.005 mm layer of zirconium oxide, such as that shown in FIG. 4b. All filters have a multi-channel construction with nineteen 4 mm straight channels for recirculation of the retentate, as shown in FIG. 1c, on the right. The thickness of the substrate is approximately 1.5 mm between channels for all filters. All filters were manufactured by Illinois Water Treatment, Inc. of Rockford, Ill.

The pore size of each of the four sample filters was rated as follows:

1) coated aluminum oxide filter; 0.2 µm nominal pore size;
2) aluminum oxide coated filter; 0.2 µm sterilizing porosity;
3) zirconium oxide coated filter; 0.1 µm nominal pore size; and
4) zirconium oxide coated filter; 0.05 µm nominal pore size.

For each test, the appropriate filter element was installed into the filter housing, and then placed into the diafiltration system. Each filter was then wetted by pumping deionized water through the system, and the system was then drained prior to each run. Seventeen liters of the liposomal feed material was added to the feed tank 12. After the diafiltration system was bled with the feed to remove air, the feed was recirculated through the filter assembly under two different operating conditions per filter tested. The operating conditions (1) and (2) are set forth in Table 7.

TABLE 7

OPERATING PARAMETERS
TESTS OF FOUR CERAMIC FILTERS

|  | recir. velocity ft/sec | mean internal channel pressure* psi | average transmembrane pressure** psi |
|---|---|---|---|
| Condition 1 | 22 | 23 | 19.5 |
| Condition 2 | 17.5 | 12.5 | 9.5 |

Each operating condition shown in Table 7 was maintained for a period of two hours during which time several measurements of the flux rate were made. For this testing, all of the filtrate was returned to the retentate, so that the composition of the retentate remained essentially unchanged over the course of the tests. This procedure is referred to as "one-hundred percent recycle."

The average value of the flux rates measured for each test operating condition is given in Table 8, where the flux rate is given in units of milliliters of filtrate per minute per square foot of filter area.

TABLE 8

FLUX RATES
TESTS OF FOUR CERAMIC FILTERS

|  | ZIRCONIUM OXIDE COATED FILTERS | | ALUMINUM OXIDE COATED FILTERS | |
|---|---|---|---|---|
|  | 0.05 µm NOMINAL* | 0.1 µm NOMINAL | 0.2 µm STERILIZING | 0.2 µm NOMINAL |
| Condition 1 flux ml/min ft² | 38 | 88 | 43 | n/a |
| Condition 2 flux ml/min ft² | 22 | 44 | 25 | 28 |

*a nominal pore size rating

The flux rates shown in Table 8 indicate that the 0.1 µm nominal pore size zirconium coated ceramic filter gave the highest flux performance under both of the test operating conditions. Contrary to what was expected, the 0.1 µm zirconium oxide coated ceramic filter resulted in approximately twice the flux performance of either the 0.05 µm or the 0.2 µm filters. This is surprising since the highest flux rates would generally be expected from filters having a higher rated pore size, and thus the 0.2 µm filter would be expected to have a higher flux rate than the 0.1 µm filter.

The 0.05 µm pore size zirconium oxide coated ceramic filter gave a flux performance similar to the two aluminum coated filters. This is likely due to the very low pore size of the 0.05 µm pore size compared to the particle size of the liposome population, and illustrates that the selection of a suitable pore size for the filter membrane is dependent on the particle size of the product to be separated.

The amount of lipid in samples of the filtrate collected during each run was determined by the standard Bartlett Phosphate Test. At the end of each filter test, the retentate samples were collected and the amount of lipid and free gentamicin determined. In addition, the particle size of the liposomes was measured. The results are shown in Table 9.

If an appreciable amount of lipid is present in the filtrate, this is an indication of a high incidence of damage to the liposomes resulting from excessively high internal pressure within the filter. The presence of damaged or improperly formed liposomes in the retentate can be an indication of excessive internal pressure. In addition, a smaller than expected population of fully formed liposomes in the retentate is also a indication of the effectiveness of the filtering operation, in which temperature and the amount of shear are also important parameters. Table 9 sets forth the results of the assays on the retentate and filtrate from each filter test. The results indicate that all four filters tested perform the desired separation acceptably, without damage to the liposome product.

TABLE 9

ASSAY RESULTS ON TESTS OF FOUR CERAMIC FILTERS

|  | COATED | | | UNCOATED |
| --- | --- | --- | --- | --- |
|  | 0.05 μM NOMINAL | 0.1 μM NOMINAL | 0.2 μM STERILIZING | 0.2 μM NOMINAL |
| FILTRATE Avg. Lipid (mg/ml) | 0.0095 | 0.0090 | 0.0053 | 0.0063 |
| RETENTATE Lipid (mg/ml) | 55.8 | 54.3 | 52.0 | 56.1 |
| Total gentamicin (mg/ml) | 20.2 | 17.5 | 16.6 | 15.3 |
| % of Free gentamicin | 54.4 | 60.3 | 53.4 | 54.3 |
| Average Particle Size (μm) | 4.3 | 4.0 | 3.2 | 3.1 |

EXAMPLE 3

Fifteen liters of liposomes having gentamicin associated therewith and prepared as in Example 1 were employed for each of two pilot-scale diafiltration tests. A diafiltration system of the type illustrated in FIG. 6 was used for the separation. For the first of the two tests, the filter assembly was equipped with two nominal 0.1 μm pore size zirconium oxide coated aluminum oxide ceramic filter elements (total filter surface area of 4.2 ft²). The filters were manufactured by Illinois Water Treatment, Inc. of Rockford, Ill., and are of the same composition as the 0.1 μm zirconium coated ceramic filter described in Example 2.

For the second diafiltration test, the filter assembly was equipped with two aluminum oxide coated aluminum oxide filters, one of 0.2 μm nominal pore size, and the other, 0.2 μm sterilizing rated pore size (total filter surface area of 4.2 ft²). The filters were manufactured by Illinois Water Treatment, Inc. of Rockford, Ill., and are of the same composition as the two aluminum oxide coated filters described in Example 2.

Diafiltration was performed to remove unassociated gentamicin from the two samples of liposome associated gentamicin. Continuous diafiltration was conducted, that is, normal saline (0.9% NaCl) was added to the liposomal formulation at the same rate at which the filtrate was being produced, maintaining fifteen liters constant volume in the system. Diafiltration was performed until 3.3 to 3.5 times the batch volume of saline was added. Both tests were run under the same filtration operating conditions: room temperature operation, recirculation velocity of 15.6 ft/sec, mean internal channel pressure of 20–21 psi, and mean transmembrane pressure of 19–20 psi. The flux rate of the filtrate was measured at least hourly during each run, and the total time of diafiltration was recorded. The filtrate and retentate were sampled at least hourly for assays to assess product integrity and effectiveness of the separation.

The results are set forth in Table 10.

TABLE 10

FLUX AND ASSAY RESULTS OF DIAFILTRATION TESTS

|  | 0.1 μm ZIRCONIUM OXIDE COATED FILTERS | 0.2 μm ALUMINUM OXIDE COATED FILTERS |
| --- | --- | --- |
| FLUX ml/min ft² | 69–74.5 | 35.7–27.4 (decreases) |
| TOTAL TIME to Complete Diafiltration, hours | 2.8 | 6.5 |
| ASSAY RESULTS | | |
| FILTRATE Avg. Lipid (mg/ml) | 0.001–0.007 | 0.001–0.004 |
| RETENTATE Lipid (mg/ml) | 58–66 | 66–83 |
| Final Ratio Lipid: Gentamicin (by wt.) | 13.3 | 11.9 |
| Final Percent Associated Gentamicin | 6.0 | 4.1 |
| Final Mean Particle Size (μm) | 3.4 | 3.6 |

The results show that flux rate using the 0.1 μm zirconium oxide coated filters was at least twice that for the 0.2 μm aluminum oxide coated filters. As a result of the superior flux performance of the 0.1 μm zirconium oxide coated ceramic filters, total diafiltration time was halved as compared to the aluminum oxide coated filters. This result was unexpected since, as a general matter, larger pore sizes allow for higher flux rates. Additionally, the results show that both the 0.1 μm zirconium oxide coated filters and the 0.2 μm aluminum oxide coated filters satisfactorily perform the desired separation (as reflected by lipid concentration in the retentate vs. filtrate), and produce a satisfactory finished diafiltered product. Nonetheless, the use of zirconium oxide filters is preferred over aluminum oxide filters since, for example, the zirconium oxide membrane can more easily be manufactured as a thinner membrane than the aluminum oxide, and, all other parameters being equal, a thinner membrane provides for a better flux rate by creating less resistance to flow.

We claim:

1. A method of separating liposomes or lipid complexes from a fluid containing the same comprising passing the fluid through a composite filter and retaining the liposomes or lipid particles, wherein the filter comprises a ceramic substrate comprising pores having an average size and a ceramic membrane comprising pores having an average size, wherein the substrate is thicker than the membrane, wherein the membrane has an average pore size of from about 0.1 microns to about 0.2 microns, wherein the membrane average pore size is less than the substrate average pore size, wherein there is a transmembrane pressure of from about 5 psi to about 35 psi, and wherein the liposomes or lipid complexes comprise a bioactive agent.

2. The method of claim 1 wherein the substrate comprises more than one layer.

3. The method of claim 1 wherein the membrane comprises more than one layer.

4. The method of claim 1 wherein the substrate ceramic is an aluminum oxide ceramic.

5. The method of claim 1 wherein the membrane ceramic is selected from the group consisting of aluminum oxide, zirconium oxide and titanium oxide ceramics.

6. The method of claim 1 wherein the membrane ceramic is a zirconium oxide ceramic.

7. The method of claim 1 wherein the thickness of the membrane is from about 0.002 to about 0.005 mm.

8. The method of claim 1 wherein the thickness of the substrate is from about 1.0 to about 2.0 mm.

9. The method of claim 1 wherein an average transmembrane pressure of the filter is about 20 p.s.i.

10. The method of claim 1 wherein the fluid has a recirculation cross-flow velocity of from about 3 to about 7 m/sec.

11. The method of claim 1, wherein the filter has a transmembrane pressure of about 6–8 psi.

12. The method of claim 1, wherein the fluid flows tangential to the filter and wherein the retentate contains the liposomes or lipid complexes.

* * * * *